US006217866B1

(12) United States Patent
Schlessinger et al.

(10) Patent No.: US 6,217,866 B1
(45) Date of Patent: Apr. 17, 2001

(54) MONOCLONAL ANTIBODIES SPECIFIC TO HUMAN EPIDERMAL GROWTH FACTOR RECEPTOR AND THERAPEUTIC METHODS EMPLOYING SAME

(75) Inventors: Joseph Schlessinger, New York, NY (US); David Givol, Rehovot (IL); Francoise Bellot, Fresnes (FR); Richard Kris, Tucson, AZ (US); George A. Ricca, Blue Bell, PA (US); Christopher Cheadle, West Chester, PA (US); Victoria J. South, Audubon, PA (US)

(73) Assignee: Rhone-Poulenc Rorer International (Holdings), Inc., Greenville, DE (US)

(*) Notice: Subject to any disclaimer, the term of this patent is extended or adjusted under 35 U.S.C. 154(b) by 0 days.

(21) Appl. No.: 08/487,761

(22) Filed: Jun. 7, 1995

Related U.S. Application Data

(63) Continuation of application No. 08/086,411, filed on Jun. 29, 1993, now abandoned, which is a continuation-in-part of application No. 07/760,852, filed on Sep. 17, 1991, now abandoned, which is a continuation-in-part of application No. 07/244,737, filed on Sep. 15, 1988, now abandoned, which is a continuation of application No. 07/319,109, filed on Mar. 3, 1989, now abandoned.

(51) Int. Cl.$^7$ .................... A61K 39/395; C07K 16/28
(52) U.S. Cl. .................... 424/143.1; 424/130.1; 424/138.1; 424/141.1; 424/152.1; 424/155.1; 424/156.1; 530/388.1; 530/388.2; 530/388.22; 530/388.8; 530/388.85
(58) Field of Search .................... 424/130.1, 138.1, 424/141.1, 143.1, 152.1, 155.1, 156.1; 530/388.1, 388.2, 388.22, 388.8, 388.85

(56) References Cited

U.S. PATENT DOCUMENTS 5,770,195    6/1998   Hudziak et al. .

OTHER PUBLICATIONS

Mendelsohn CMBT 307–312, 1988.*
Harris TIBTECH 14: p. 42–44, 1993.*
Osbard, Immunology Today 11:193, 1990.*
Waldman, Science 252:1657, 1991.*
Aboud–Pirak PNNAS 86:3778 May 1989.*
Aboud–Pirak JNCI 80:1605, 1988.*
Ennis, J. Cell Biochem, Suppl 13B:104, 1989.*
Murthy, Arch. Biochem, Biophy 252:549, 1987.*
Hird, Genes & Cancer, Carry et al Ed, John Wiley 183–189, 1990.*
Epenetos, Br. Med. J 290:1463, 1985.*
Mendelsohn, "Epidermal Growth Factor Receptor Inhibition by a Monoclonal Antibody as Anticancer Therapy," Clinical Cancer Research 3, 2703–2707, (1997).
Prewett, et al. "The Biological Effects of C225, A Chimeric Monoclonal Antibody to the EGFR, on Human Prostate Carcinoma," Journal of Immunotherapy, 19, 419–427 (1997).

* cited by examiner

Primary Examiner—Nancy A. Johnson
(74) Attorney, Agent, or Firm—Hoffmann & Baron, LLP; Irving N. Feit

(57) ABSTRACT

Hybridoma cell lines producing monoclonal antibodies specific to the human epidermal growth factor receptor are disclosed. The antibodies are capable of inhibiting the growth of human tumor cells expressing human epidermal growth factor receptors. Therapeutic uses of these monoclonal antibodies by themselves and in combination with anti-neoplastic agents are also disclosed.

9 Claims, 17 Drawing Sheets

FIG. 1 THE EFFECT OF mAb 108.4, DOXORUBICIN AND THEIR COMBINATION

FIG. 2 THE EFFECT OF 108.4 mAb, cis-DDP AND THEIR COMBINATION

```
            1
          Met Asp Val                              117
                                                 Ala Ala   *
ACC ATG GAT GTT                       GCT GCA TGA GGA TCC
    NcoI                                              BamH1
(SEQ ID NO: 3)                                   (SEQ ID NO: 4)
```

96 V_H

```
            1
          Met Glu Val                              118
                                                 Ser Ala   *
ACC ATG GAA GTG                       TCT GCA TGA GGA TCC
    NcoI                                              BamH1
(SEQ ID NO: 5)                                   (SEQ ID NO: 6)
```

108 V_L

```
            1
          Met Glu Ile                              112
                                                 Ala Ala   *
ACC ATG GAA ATC                       GCT GCA TGA GGA TCC
    NcoI                                              BamH1
(SEQ ID NO: 7)                                   (SEQ ID NO: 8)
```

108 V_H

```
            1
          Met Gln Val                              121
                                                 Ser Ser   *   *
ACC ATG CAG GTT                       TCC TCC TAA TAA GGA TCC
    NcoI                                              BamH1
(SEQ ID NO: 8)                                   (SEQ ID NO: 9)
```

```
  1 CAG GTT CAG CTG CAG CAG TCT GGA GCT GAG CTG ATG AAG CCT GGG
  1 Gln Val Gln Leu Gln Gln Ser Gly Ala Glu Leu Met Lys Pro Gly

CDR 1
 46 GCC TCA GTG AAG ATA TCC TGC AAG GCT ACT GGC TAC ACA TTC AGT
 16 Ala Ser Val Lys Ile Ser Cys Lys Ala Thr Gly Tyr Thr Phe Ser

91 AGT TAC TGG ATA GAG TGG GTA AAG CAG AGG CCT GGA CAT GGC CTT
 31 Ser Tyr Trp Ile Glu Trp Val Lys Gln Arg Pro Gly His Gly Leu
                                                CDR 2
136 GAG TGG ATT GGA GAG ATT TTA CCG GGA AGT AAA AAA ACT AAC TAC
 46 Glu Trp Ile Gly Glu Ile Leu Pro Gly Ser Lys Lys Thr Asn Tyr

181 AAT GAG AAG TTC AAG GGA AAG GCC ACA TTC ACT GCA GAT ACA TCC
 61 Asn Glu Lys Phe Lys Gly Lys Ala Thr Phe Thr Ala Asp Thr Ser

226 TCC AAC ACA GCC TAC ATG CAA TTT AGC AGC CTG ACA TCT GAG GAC
 76 Ser Asn Thr Ala Tyr Met Gln Phe Ser Ser Leu Thr Ser Glu Asp
                                                        CDR 3
271 TCT GCC GTC TAT TAC TGT GCA AGA TAT TAC TAT AGG AAC GAC GAC
 91 Ser Ala Val Tyr Tyr Cys Ala Arg Tyr Tyr Tyr Arg Asn Asp Asp

316 TAT GGT ATG GAC TAC TGG GGT CAA GGA ACC TCA GTC ACC GTC TCC
106 Tyr Gly Met Asp Tyr Trp Gly Gln Gly Thr Ser Val Thr Val Ser

361 TCA
121 Ser
```

```
  1 GAA ATC CAC ATG ACA CAG ACT ACA TCC TCC CTG TCT GCC TCT CTG
  1 ▲Glu Ile His Met Thr Gln Thr Thr Ser Ser Leu Ser Ala Ser Leu
                                                            CDR 1
 46 GGA GAC AGA GTC ACC ATC AGT TGC AGT GCA AGT CAG GAC ATC AGG
 16 ▲Gly Asp Arg Val Thr Ile Ser Cys Ser Ala Ser Gln Asp Ile Arg

91 AAT TAT TTA AAC TGG TAT CAG CAG AAA CCT GAT GGA ACT GTT AAA
 31 ▲Asn Tyr Leu Asn Trp Tyr Gln Gln Lys Pro Asp Gly Thr Val Lys
                                                    CDR 2
136 CTC CTG ATC TAT TAC ACA TCA ACT TTA CAT TCA GGA GTC CCA TCA
 46 ▲Leu Leu Ile Tyr Tyr Thr Ser Thr Leu His Ser Gly Val Pro Ser

181 AGG TTC AGT GGC AGT GGG TCT GGG ACA GAT TAT TCT CTC ACC ATC
 61 ▲Arg Phe Ser Gly Ser Gly Ser Gly Thr Asp Tyr Ser Leu Thr Ile

226 AGC AAC CTG GAA CCT GAA GAT ATT GCC ACT TAT TAT TGT CAG CAG
 76 ▲Ser Asn Leu Glu Pro Glu Asp Ile Ala Thr Tyr Tyr Cys Gln Gln
                              CDR 3
271 TAT AGT AAG ATT CCG TAC ACG TTC ACA GGG GGG ACC AAG CTG GAA
 91 ▲Tyr Ser Lys Ile Pro Tyr Thr Phe Thr Gly Gly Thr Lys Leu Glu

316 ATA AAA|CGG GCT GAT GCT GCA
106 ▲Ile Lys|Arg Ala Asp Ala Ala
```

```
  1 GAA GTG CAG CTG GTG GAG TCT GGG GGA GGA TTA GTG AGG CCT GGA GGG
  1 Glu Val Gln Leu Val Glu Ser Gly Gly Gly Leu Val Arg Pro Gly Gly

49 TCC CTG AAA CTC TCC TGT GCA GCC TCT GGA TTC GCT TTC AGT AAC TAT
 17 Ser Leu Lys Leu Ser Cys Ala Ala Ser Gly Phe Ala Phe Ser Asn Tyr
                                                    CDR 1

97 GAC ATG TCT TGG GTT CGC CAG ACT CCG GAG AAG AGG CTG GAG TGG GTC
 33 Asp Met Ser Trp Val Arg Gln Thr Pro Glu Lys Arg Leu Glu Trp Val

145 GCG TAC ATT GGT AAT GGT GGT AAC ACC TAC TCT CCA GAC ACT GTG AAG
 49 Ala Tyr Ile Gly Asn Gly Gly Asn Thr Tyr Ser Pro Asp Thr Val Lys
                                    CDR 2

193 GGC CGA TTC ACC ATC TCC AGA GAC AAT GCC GAG AAC ACC CTA TAC CTT
 65 Gly Arg Phe Thr Ile Ser Arg Asp Asn Ala Glu Asn Thr Leu Tyr Leu

241 CAA ATG AGC AGT CTG AAG TCT GAG GAC ACA GCC ATT TAT TAC TGT GCA
 81 Gln Met Ser Ser Leu Lys Ser Glu Asp Thr Ala Ile Tyr Tyr Cys Ala

289 AGT CAC TAT GGT TAC GAC GGG AGG TTT GCT TAC TGG GGC CAA GGG ACT
 97 Ser His Tyr Gly Tyr Asp Gly Arg Phe Ala Tyr Trp Gly Gln Gly Thr
                         CDR 3

337 CTG GTC ACT GTC TCT GCA
113 Leu Val Thr Val Ser Ala
```

```
  1  GAT GTT GTG ATG ACC CAA AGT CCA CTC TCC CTG CCT GTC AGT
  1 ▲Asp Val Val Met Thr Gln Ser Pro Leu Ser Leu Pro Val Ser

43  CTT GGA GAT CAA GCC ACC ATC TCT TGC AGA TCT AGT CAG AGC
 15 ▲Leu Gly Asp Gln Ala Thr Ile Ser Cys Arg Ser Ser Gln Ser
        CDR 1
 85  CTT GAA CAC AGT AAT GGA GAC ACC TAT TTA CAT TGG TAC CTG
 29 ▲Leu Glu His Ser Asn Gly Asp Thr Tyr Leu His Trp Tyr Leu

127  CAG AAG GCA GGC CAG TCT CCA AAG CTC CTG ATC TAC AAA GTT
 43 ▲Gln Lys Ala Gly Gln Ser Pro Lys Leu Leu Ile Tyr Lys Val
        CDR 2
169  TCC AAC CGA TTT TCT GGG GTC CCG GAT AGG TTC AGT GGC AGT
 57 ▲Ser Asn Arg Phe Ser Gly Val Pro Asp Arg Phe Ser Gly Ser

211  GGA TCA GGG ACA GAT TTC ACA CTC AAG ATC AGC AGA GTG GAG
 71 ▲Gly Ser Gly Thr Asp Phe Thr Leu Lys Ile Ser Arg Val Glu
                                                        CDR 3
253  GCT GAG GAT CTG GGA GTT TAT TTC TGC CAA AGT ACA CAT
 85 ▲Ala Glu Asp Leu Gly Val Tyr Phe Cys Gln Ser Thr His

295  GTT CCG TGG ACG TTC GGT GGA GGC ACC AAG CTG GAA ATC AAA
 99 ▲Val Pro Trp Thr Phe Gly Gly Gly Thr Lys Leu Glu Ile Lys

337  CGG GCT GAT GCT GCA
  1  Arg Ala Asp Ala Ala
```

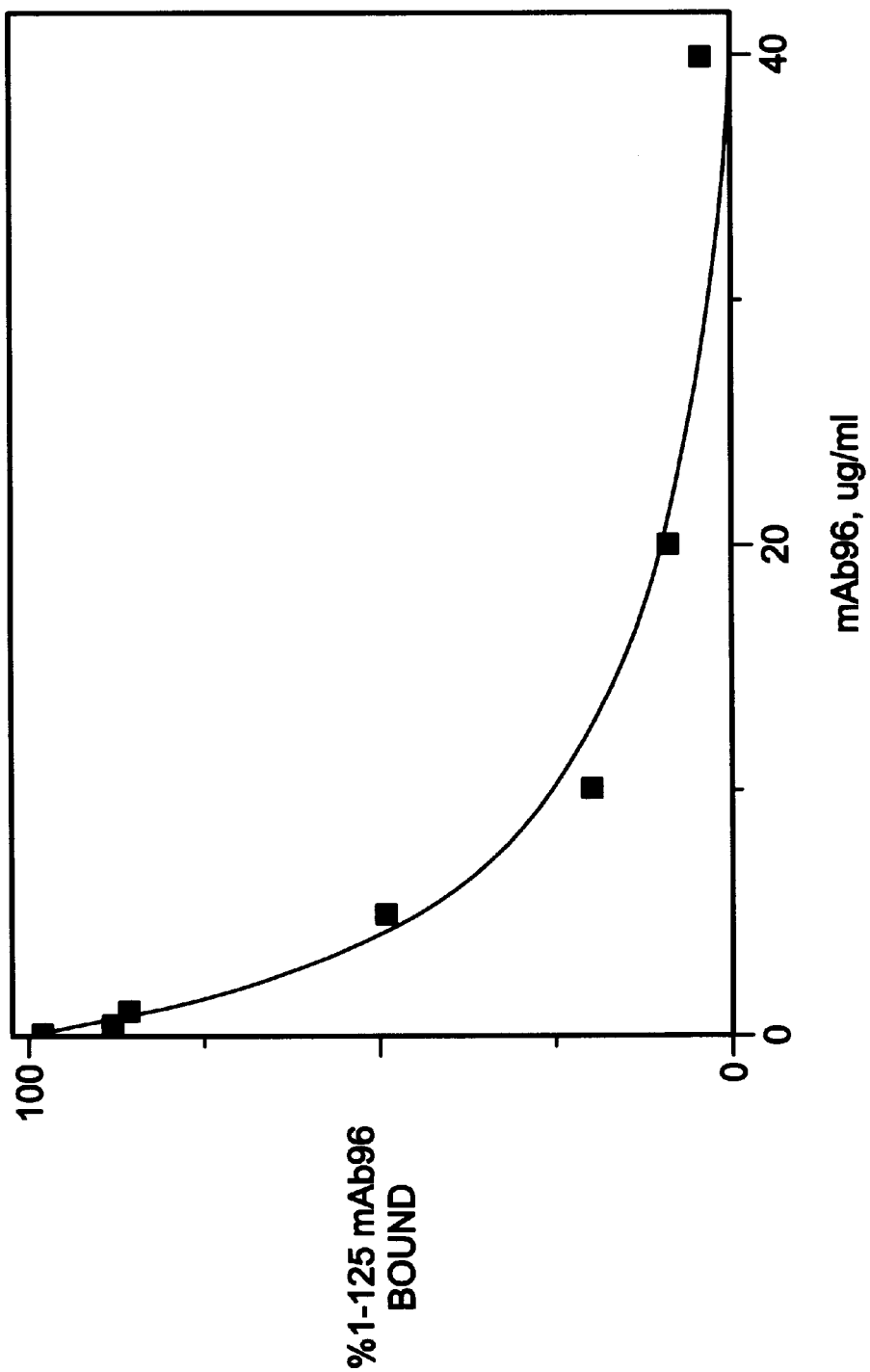
FIG. 14 mAb96 COMPETITION / IODINATED mAb96 VS mAb96

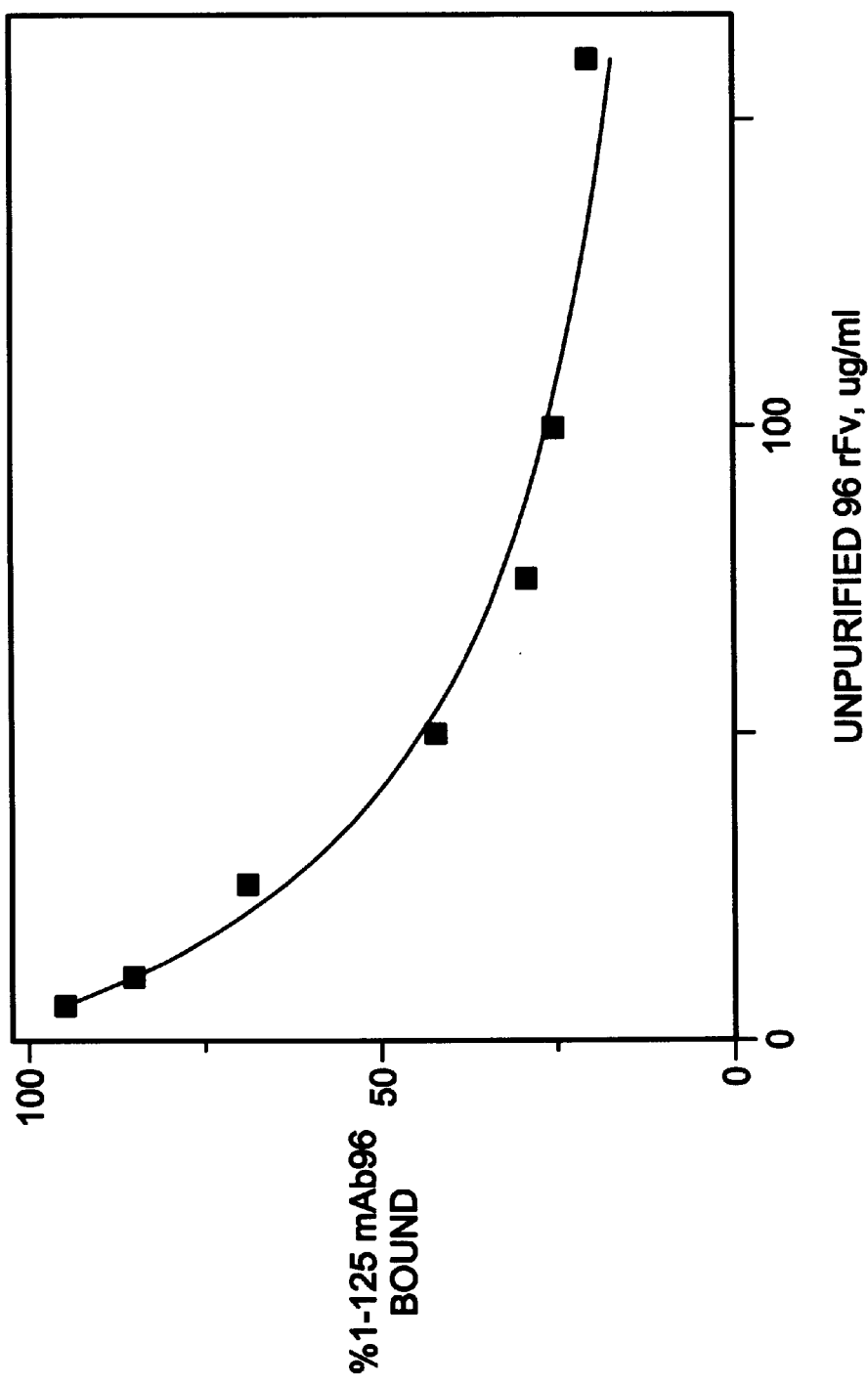
FIG. 15 96 rFv COMPETION / IODINATED mAbB96 VS 96 rFv

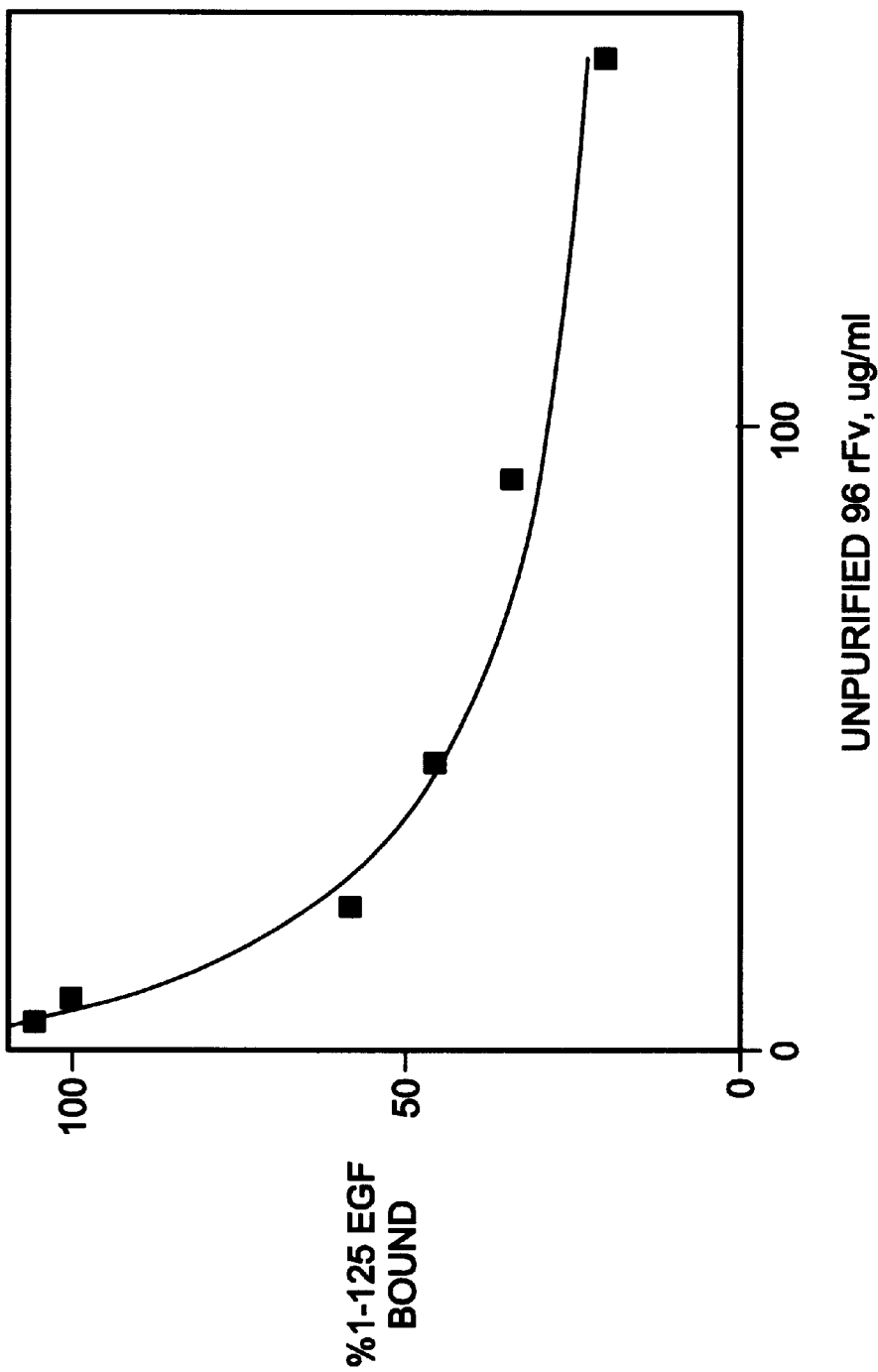
FIG. 16  96 rFv COMPETITION / IODINATED EGF VS 96 rFv

MONOCLONAL ANTIBODIES SPECIFIC TO HUMAN EPIDERMAL GROWTH FACTOR RECEPTOR AND THERAPEUTIC METHODS EMPLOYING SAME

RELATED APPLICATIONS

This is a continuation of application Ser. No. 08/086,411 filed on Jun. 29, 1993, now abandoned, which is a continuation-in-part of U.S. application Ser. No. 07/760,852, filed Sep. 17, 1991 now abandoned, which is a continuation-in-part of Ser. No. 07/244,737, filed Sep. 15, 1988, now abandoned, and a continuation of Ser. No. 07/319,109, filed Mar. 3, 1989, now abandoned.

BACKGROUND OF THE INVENTION

This invention relates to new hybrid cell lines and in particular to hybrid cell lines for production of monoclonal antibodies specific to a human receptor for epidermal growth factor (EGF) which can inhibit the growth of human tumor cells that express human EGF receptors, to the antibodies so produced, to therapeutic methods employing the antibodies, and to therapeutic methods employing the antibodies in combination with anti-neoplastic agents.

Control of cell growth is regulated by the interaction of soluble growth factors and cell membrane receptors.

The first step in the mitogenic stimulation of epidermal cells is the specific binding of epidermal growth factor (EGF) to a membrane glycoprotein known as the epidermal growth factor receptor (EGF receptor). (Carpenter, et al., Epidermal Growth Factor, *Annual Review Biochem.,* Vol. 48, 193–216 (1979)). The EGF receptor is composed of 1,186 amino acids which are divided into an extracellular portion of 621 residues and a cytoplasmic portion of 542 residues connected by a single hydrophobic transmembrane segment of 23 residues. (Ullrich et al., Human Epidermal Growth Factor cDNA Sequence and Aberrant Expression of the Amplified Gene in A-431 Epidermoid Carcinoma Cells, *Nature,* Vol. 309, 418–25 (1986)). The external portion of the EGF receptor can be subdivided into four domains. Recently, it has been demonstrated that domain III, residues 333 to 460, which is flanked by two cysteine domains is likely to contain the EGF binding site of the receptor. (Lax, et al., Localization of a Major Receptor-Binding Domain for Epidermal Growth Factor by Affinity Labeling, *Mol. and Cell Biol.,* Vol. 8, 1831–1834 (1988)). The binding of EGF to domain III leads to the initiation of pleiotropic responses leading to DNA synthesis and cell proliferation.

It has been found in various types of human tumor cells that those cells overexpress EGF receptors. For example, the cancerous cells of bladder tumors have been shown to have a relatively large population of EGF receptors. (Neal et al., Epidermal Growth Factor Receptor in Human Bladder Cancer: Comparison of Invasive and Superficial Tumors, *Lancet,* Vol. 1, 366–367 (1985)). Breast cancer cells exhibit a positive correlation between EGF receptor density and tumor size and a negative correlation with the extent of differentiation. (Sainsbury et al., Epidermal Growth Factor Receptors and Oestrogen Receptors in Human Breast Cancer. *Lancet,* Vol. 1, 364–366 (1985); Presence of Epidermal Growth Factor Receptor as an Indicator of Poor Prognosis In Patients With Breast Cancer. *J. Clin. Path.,* Vol. 38, 1225–1228; Epidermal-Growth-Factor Receptor Status as Predictor of Early Recurrence and Death From Breast Cancer. *Lancet,* Vol.1, 1398–1400 (1987). The tumorigenicity of a series of human vulval epidermoid carcinoma (A431) clonal variants implanted into athymic mice having different levels of EGF receptors was found to correlate directly with the level of expression of the EGY receptor (Santon et al., Effects of Epidermal Growth Factor Receptor Concentration on Tumorigenicity of A431 cells in nude mice. *Cancer Res.,* Vol. 46, 4701–4700 (1986)). Thus, it has been proposed that overexpression of EGF receptors play a role in the origin or tumorigenesis of cancer cells.

The influence of EGF receptor density on the biological behavior of cancer cells may be mediated by the interaction of the receptor with its ligands—namely, EGF or transforming growth factor (TGF). In the majority of cells, when EGF binds to a specific region of the EGF receptor, the cell is mitogenically stimulated. Other tumor cells, such as A431 cells are not mitogenically stimulated by the binding of EGF to its receptors.

Two groups have reported in vivo growth inhibition of tumor A431 cell xenografts in nude mice by binding monoclonal antibodies to the epidermal growth factor receptor of the tumorous cells. Masui et al. demonstrated that treatment with anti-EGF receptor monoclonal antibodies of the IgG2a and IgGI isotype completely prevented tumor formation in athymic mice by subcutaneously implanted A431 cells when treatment was started on the day of tumor cell inoculation. (Masui et al., Growth Inhibition of Human Tumor Cells in Athymic Mice by Anti Epidermal Growth Factor Receptor Monoclonal Antibodies. *Cancer Res.,* Vol. 44 1002–1007 (1984); Mechanism of Antitumor Activity in Mice for Anti Epidermal Growth Factor Receptor Monoclonal Antibodies With Different Isotypes. *Cancer Res.* Vol. 46 5592–5598 (1986)). Rodeck et al. used a different monoclonal antibody than Masui of the IgG2a isotype which also binds to the EGF receptor of A431 cells to completely inhibit tumor growth of A431 cells xenotransplanted in mice. (Rodeck et al. Tumor Growth Modulation by a Monoclonal Antibody to the Epidermal Growth Factor Receptor: Immunologically Mediated and Effector Cell—Independent Effects. *Cancer Res.,* Vol. 47, 3692–3696 (1987)).

To date, no one, however, has inhibited the in vitro or in vivo growth of human oral epidermoid carcinoma (KB) or human mammary epithelial (184AIN4 and 184AIN4-T—collectively "184") cells. KB and 184 cells are commonly used in studies relating to the EGF-receptor.

KB and 184 cells are substantially different from A431 cells, especially in terms of their growth response to epidermal growth factor. KB and 184 cells are growth stimulated by high concentrations of epidermal growth factor whereas A431 cells are growth inhibited by high concentrations of epidermal growth factor.

Those differences as well as the lack of complete understanding of the mechanism by which the anti-EGF-receptor antibodies inhibit the growth of tumor cells in vivo, prohibit one from accurately determining whether monoclonal antibodies which bind to EGF receptor of A431 cells and demonstrate anti-tumoral activity on A431 cell xenografts in nude mice will also demonstrate antitumoral activity on KB or 184 cell xenografts in nude mice.

Additionally, because human tumor cells are also growth stimulated by epidermal growth factor, KB and 184 cells provide a more representative pattern of responding to EGF than A431 cells, and, in fact, are used as a model for human tumor cells expressing EGF receptors. (Willington et al. *J Cell Biol.,* Vol. 94, 207–212 (1982).

The primary goal in treating tumors is to kill all the cells of the tumor. A therapeutic agent that kills the cell is defined as cytotoxic. A therapeutic agent that merely prevents the cells from replicating, rather than killing the cells, is defined as cytostatic.

Treatment solely with monoclonal antibodies which bind to the EGF receptor merely prevent the cells from replicating, and thus, the monoclonal antibodies act as a cytostatic agent. In order to overcome the monoclonal antibody's cytostatic limitations, monoclonal antibodies specific to the extracellular domain of human epidermal growth factor receptors have been combined with macrophage or mouse complement to yield a cytotoxic response against A431 cells. (Masui et al., Mechanism of Antitumor Activity in Mice for Anti-Epidermal Growth Factor Receptor Monoclonal Antibodies with Different Isotopes, *Cancer Research,* Vol. 46, 5592–5598 (1986)).

Anti-neoplastic or chemotheropeutic agents administered by themselves, are effective cytotoxic agents. The use of anti-neoplastic agents such as doxorubicin (adriamycin) and cisplatin, for example, are well known in the art. Use of those reagents by themselves, however, are only effective at levels which are toxic or subtoxic to the patient. Cisplatin is intravenously administered as a 100 mg/m$^2$ dose once every four weeks and adriamycin is intravenously administered as a 60–75 mg/m$^2$ dose one every 21 days.

Bacterial Expression of Antibodies: The prototypical immunoglobulin structure consists of a 150,000 dalton heterodimer composed of two heavy (50,000 daltons each) and two light (25,000 daltons each) chains. Each heavy and light chain pair are covalently attached by a disulfide bond located between the first and second constant domains that joins the carboxy terminal end of the light chain with the heavy chain. The two heavy and light chain pairs are themselves joined together by one or more disulfide bonds, referred to as the hinge region, located between the two heavy chains [1]. Thus, bacterial expression of an entire active immunoglobulin molecule requires, 1) the complex refolding of both heavy and light chains, 2) the concomitant formation of up to 16 disulfide bonds, and 3) the association of protein dimers to form the final divalent molecule.

Initial attempts to produce antibodies in *E. coli* focused on the expression of entire heavy and light chains, either separately or together in the same cell line [2, 3]. Low levels of expression for both chains were reported in 1984 by two separate groups. Cabilly et al. [2] working with an anti-carcinoembryonic antigen antibody (CEA) reported expression levels of 3% and 0.5% (percent of total cellular protein) for heavy and light chains, respectively. Boss et al. [3] working with an anti-4-hydroxy-3-nitrophenyl acetyl (NP) antibody was able to express the light chain (13% of total protein) in a protease deficient cell line (K12 strain E103S) but the same system only yielded 1% heavy chain. Despite these difficulties with expression levels, both groups reported the first successful recovery of antibody activity from genes cloned and expressed in *E. coli.*

Specific antigen binding activity was detected by both groups following reduction, denaturation, and refolding (in the presence of redox reagents) of partially purified chains. No active antibody was detected in a mixture of heavy and light chain whole cell extracts, nor observed in a lysate made from cells coproducing the two chains together [2]. Reported recoveries of activity from the refolding procedures range from 3–5% for the anti-CEA antibody down to as low as 0.007% for the anti-NP antibody. Cabilly found similarly low levels of recovery (0.5%) using native anti-CEA antibody subjected to the same denaturation and renaturation procedures [2]. In addition, Boss observed that the majority of active anti-NP material contained truncated heavy chains, suggesting that the shorter peptides were somehow favored during the refolding process [3]. Finally, the actual formation of complete heterodimeric antibodies remains in doubt since no evidence was obtained for divalency by either group.

Fortunately, it is not necessary to express an entire antibody molecule in order to reproduce its antigen-binding capacity. Native antibody protein can be proteolytically degraded under controlled conditions to yield a number of different fragments, some of which retain the full antibody binding capacity. Digestion with the enzyme papain cleaves the heavy chain peptides at a point between the hinge region and the disulfide bond connecting the heavy and light chains. The resulting fragment, referred to as an Fab, is monovalent with respect to its antigen-binding site. The Fab fragment retains an entire light chain, as well as one-half of a heavy chain, with both chains covalently linked by the carboxy terminal disulfide bond.

Inbar et al., [4] used a mouse IgA-myeloma protein (MOPC315) to demonstrate that an Fab fragment could be further cleaved by pepsin digestion, to yield an even smaller antigen binding fragment. This fragment, referred to as an Fv, has an approximate molecular weight of 25,000 daltons and is composed of the amino terminal variable regions of the heavy and light chains ($V_H$ and $V_L$, respectively) held together by non-covalent bonds. The Fv fragment was shown to retain the same binding specificity for 2,4-dinitrophenyl (DNP) as well as the same affinity (Kd=4× 10$^{-7}$M) as the intact antibody.

Efficient production of antibody fragments in bacteria would appear to be less difficult for Fvs than for the larger fragments or for complete antibodies. Protein refolding is simplified since each active $V_H$ or $V_L$ chain is required to form a single globular domain stabilized by one intrachain disulfide bond. The association of the two chains in an active Fv requires noncovalent interactions only and occurs with a Kd greater than 10$^{-8}$ M for MOPC315 Fv [5].

The work of Hochman et al. [5] predicts that it should be possible to recombine separately expressed MOPC315 $V_H$ and $V_L$ chains to form active Fv molecules in an efficient manner. They used purified MOPC315 Fv, denatured in 8M urea, to isolate individual $V_H$ and $V_L$ chains by DEAE-cellulose chromatography [6]. The inactive $V_H$ and $V_L$ chain components were recombined to form an active Fv following a simple and efficient (80–90% recovery) refolding procedure. In addition, it was shown that active Fv could be recovered efficiently from reduced as well as denatured material [5]. Since it can be anticipated that reduction as well as denaturation will be required to solubilize and purify overexpressed proteins from *E. coli,* it is useful to note that neither reduction nor denaturation of native MOPC315 $V_H$ and $V_L$ chains prior to refolding prevented efficient recoveries of the native Fv [5].

The results of these early experiments were encouraging to the extent that they confirmed the possibility of producing recombinant antibody molecules in *E. coli.* Clearly, however, the low levels of expression in combination with low yields of active material indicated that further efforts would be required for efficient bacterial production of antigen-binding proteins.

Bicistronic Constructs: As a result of the inherent difficulties in recovering active whole antibody chains from *E. coli,* efforts were directed towards the microbial expression and recovery of active Fv or Fab antibody fragments. Success in these efforts was achieved both in yeast and in bacteria. Recovery of active antibody Fv fragments from *E. coli* has since been reported using several different strategies.

Initial success was achieved by two separate groups who reported the recovery of secreted active antibody fragments from *E. coli* by co-expressing the two chains of either an Fv [7] or an Fab [8] on the same plasmid. Both bicistronic constructs were characterized by a joint expression of separate heavy and light chain fragment genes under the direction of a single transcriptional unit. This co-expression allows for the synthesis of approximately stoichiometric amounts of both chains. Translation and refolding of each chain occurs in close proximity to each other within the cell. In addition, each peptide coding region has been engineered for secretion by the addition of an amino terminal bacterial leader sequence, directing the expressed products through the inner membrane to the bacterial periplasm. This membrane translocation mimics the processing of eukaryotic protein into the lumen of the endoplasmic reticuluum (ER), a process which occurs normally during the immunoglobulin assembly process in mammalian B cells [1]. The passage of the recombinant proteins across the *E. coli* membrane was predicted to be functionally analogous to ER transport, facilitating proper refolding and disulfide formation of antibody fragment molecules [7].

Active antigen-binding fragments were, in fact, isolated by both groups either from the periplasm [7] or directly from the culture medium [8]. Skerra and Plückthun used a bicistronic construct in which bacterial signal sequences for outer membrane protein A (ompA) and alkaline phosphatase (phoA) were fused to synthetic genes encoding the $V_H$ and $V_L$ domains of McPC603, an anti-phosphorylcholine (PC) mouse IgA antibody [9]. Expression was driven by an isopropyl-β-D-thiogalactoside (IPTG) inducible lac promoteroperator. Active Fv fragments could be rapidly purified to homogeneity by phosphorylcholine affinity chromatography of periplasmic fractions. Typical yields were reported to be approximately 0.2 mg of purified Fv fragment per liter of bacterial culture. Measurements of the affinity of the recombinant Fv gave results identical to the corresponding affinity of native McPC603 isolated from mouse ascites (Kd=6–8× $10^{-6}$M).

Better et al. [8] reported higher yields (2 mg/L) of active recombinant L6 Fab (a mouse—human chimeric antibody reactive against the human carcinoma cell line C3347) using a *S. typhimurium* araB (ParaB) promoter to drive the expression of a bicistronic construct containing the full-length L6 light chain and the N-terminal half of the L6 heavy chain (a truncated heavy chain of this type is referred to as an Fd), both preceded by a pectate lyase (pelB) bacterial leader sequence. This construct directed active L6 Fab to the extracellular culture medium from which it could be directly purified using sequential cation-exchange chromatography. Subsequently, the same group reported the successful recovery of active L6 whole antibody as well as Fab fragment from yeast [10].

The bicistronic construct with bacterial leader sequences has since been successfully employed by others, most notably by those involved in the construction of antibody recombinatorial libraries using polymerase chain reaction (PCR) techniques [11–13]. In brief, these libraries are constructed from a large array of individual heavy and light chain fragments, cloned by PCR amplification from a variety of biological sources such as spleen, peripheral blood lymphocyte, and hybridoma cell RNA using antibody-specific generic primers. The heavy and light chain genes are allowed to randomly assort during a subcloning procedure which finally results in the formation of a repertoire of Fab fragments arranged in bicistronic constructs expressed in bacteriophage lambda vectors. These libraries are screened with labeled antigens to identify and isolate novel antibodies. As interesting as this work has been in terms of its potential to replace hybridoma screening for the production of monoclonal antibodies (a somewhat controversial projection, see Winter and Milstein, 1991 [14]), no data has as yet been presented which demonstrates production of either recombinant active Fv or Fab in *E. coli* in significantly high yields using a bicistronic system.

Single-chain constructs: Architects of single-chain constructs have taken the bicistronic approach to the bacterial expression of antibody fragments one step further by expressing tandemly linked VH and VL genes together as a single protein. This work was pioneered by two separate groups [15, 16] using a similar system, which employs a 15–20 amino acid, neutral peptide linker to fuse the carboxy terminus of a $V_H$ or a $V_L$ gene to the N-terminus of its corresponding partner (see FIG. 20); the order of the two genes appears to be reversible. Bird et al. [16] used a series of custom designed linker sequences based on protein modeling of their projected single-chain Fvs (sFv) while Huston et al. [15] designed a more generic (Gly4, Ser)3 linker which has since been used extensively by other researchers. Both groups used standard *E. coli* promoter/operator (P/O) systems such as the hybrid, lambda leftward operator/rightward promoter (OL/PR) [16] or the tryptophan P/O [15] to drive the expression of sFv proteins in bacteria. Reported recoveries of active sFv protein were good, ranging from 5–30% of expressed protein for an anti-bovine growth hormone (BGH) sFv [16] to 13% for an anti-digoxin sFv [15].

The anti-digoxin sFv yields were later optimized to 23% and then the basic construct was modified by the N-terminal addition of the coding region for fragment B of staphylococcal protein A which binds to the Fc region of IgG [17]. The resulting bifunctional molecule (FB-sFv) was recovered at very high efficiencies (46%) and was shown to crosslink IgG to digoxin-bovine serum albumin. The successful addition of an effector domain to the amino terminus of an immunoglobulin binding region was entirely novel and has since been repeated with other Ab fragments [18–20].

Fusion of a toxin gene to the carboxy terminal end of an sFv has been reported by Chaudhary et al. [18]. The initial immunotoxin construct joined a sFv specific for the interleukin-2 receptor (anti-Tac) to a fragment of the Pseudomonas exotoxin (PE40) from which the native exotoxin binding domain was removed. The anti-Tac sFv was constructed using a (Gly4, Ser)$_3$ linker and expression of the immunotoxin was driven by the strong IPTG-inducible polymerase-specific T7 promoter [21, 22]. The resulting purified and refolded fusion protein (recovered at 0.2 mg/L) was shown to be highly cytotoxic to IL-2 receptor-bearing human cell lines but not to receptor-negative cells. This group has also reported the successful construction of several new single-chain immunotoxin proteins including one in which the coding region for a truncated form of diptheria toxin (DT) is linked to the N-terminus of the anti-Tac sFv [18]. The DT-anti-Tac sFv was shown to be as active as its anti-Tac-PE40 sFv counterpart and was recovered at significantly higher levels (3–5 mg/L).

Higher levels of recovery (10–12 mg/L, or 20% recovery) of active single-chain Ab have been reported by other researchers using the T7 promoter and a (Gly4 Ser)$_3$ linker to express a sFv specific to the major cellular receptor for human rhinovirus (ICAM-1) [23]. In general, recoveries of active protein from recombinant single-chain Abs (when reported) remain at or below 10 mg/L levels. It is not clear yet whether the apparent limit on recovery levels of most single-chain proteins is a reflection of the level of gene expression, the result of simple peptide to peptide variability, or the inherent limitations imposed by the complexity of sFv refolding.

Separate chain constructs: The expression of $V_L$ and $V_H$ chains in separate bacterial cell lines followed by recombination of purified peptides to form active Fv, is an alternate approach to either the bicistronic or single-chain strategies. Recombinant $V_L$ and $V_H$ peptides can be independently purified, recombined and refolded in vitro in a potentially efficient manner as predicted by the work on native MOPC315 Fv by Hochman et al. [6]. One major advantage of this method of Fv production includes the prospect of high levels of $V_H$ and $V_L$ peptide expression using T7 promoters. In addition, the refolding problem for each separate chain is relatively simple. It is necessary to form only one disulfide bond in a single globular domain. Bond formation in separate chains can be controlled by adjusting protein concentrations downwards during oxidation in order to form only the correct intrachain disulfide bonds. It may be possible with a combination of high levels of protein expression and enhanced refolding efficiencies to greatly reduce the effect of peptide variability on general recoveries of active Fvs.

The first report of active Fv fragments produced by separate chain expression in E. coli was included in an international patent application filed in 1988 [24]. These workers obtained moderately high levels of expression (20–140 mg/L) of mouse immunoglobulin light and heavy chain variable region peptides using an inducible tryptophan promoter/operator in protease deficient host cell lines [24]. Active Fv fragment specific for a hen egg lysozyme epitope (Gloop2) was recovered at 2% levels following partial purification and subsequent refolding of $V_H$ and $V_L$ peptides.

Baldwin and Schultz [25] have reported recovery of DNP-binding activity from a chimeric MOPC315 Fv using recombinant $V_L$ peptides associated with native $V_H$ protein. Moderate levels of $V_L$ expression (10–30 mg/L) were obtained in the form of a $V_L$ fusion protein. The MOPC315 $V_L$ coding sequence was linked via a factor Xa recognition site to the bacteriophage lambda CII protein with expression being driven by the lambda leftward promoter. The yield of $V_L$ protein following factor Xa cleavage and purification was between 5–20% and this purified $V_L$ was efficiently refolded in the presence of native $V_H$ yielding active Fv at between 20–30% efficiencies. Overall yields of active MOPC315 recombinant Fv from starting material ($V_L$ fusion protein) are therefore calculated to be between 1–6%.

Cheadle et al. [26] reported the cloning and expression of both the $V_H$ and $V_L$ of MOPC315 in E. coli using a bacteriophage T7 promoter sequence. The recombinant chains were initially recovered as inclusion bodies and then dissolved separately in 8M urea, combined together, and refolded by subsequent chaotrope removal. Biologically active Fv was affinity purified from the chain mixture by specific binding to DNP-Lysine Sepharose. Yields of active material as high as 20% were obtained with activity confirmed by fluorescence quench analysis. The purified recombinant Fv displayed a binding affinity identical to the native Fv.

Chimeric Fvs specific for 5-dimethylaminonapthalene-1-sulfonyl (Dns) have been produced using bacterially expressed VH peptides recombined with entire native light (L) chains (44). The $V_H$ chains were produced at surprisingly low levels (10 mg/L) using a T7 promoter in a T7 polymerase transient infection system (lambda phage derivative CE6 [27]). The transient T7 expression system is primarily used when the gene product has been demonstrated to be toxic to host cell growth. Purified $V_H$ was recombined with native homologous light chains and active VHL dimers were recovered with efficiencies between 1–6%.

SUMMARY OF THE INVENTION

The present invention provides for novel hybridoma cell lines, ATCC HB 9763 and 9764, each of which provides as a component of the supernatant of its growth the highly specific monoclonal antibody, 96 and 108, respectively. Cell lines ATCC HB 9763 and 9764 were deposited in the American Type Culture Collection, 12301 Parklawn Drive, Rockville, Md. 20852, a recognized public depository for strains of microorganisms on Jul. 25, 1988. The present invention provides cell lines to produce novel monoclonal antibodies which inhibit the growth of human tumor cells that express human EGF receptor by binding specifically to the EGF receptor found on the cell membrane of the tumor cells.

An object of this invention is to provide two cell lines, each of which produces a novel monoclonal antibody that inhibits the growth of human tumor cells by the antibody binding to the extra-cellular domain of the human EGF receptors of the tumor cells in an antigen-antibody complex, wherein the tumor cells are characterized by their expression of human EGF receptors and mitogenic stimulation by EGF. The monoclonal antibodies are further characterized by their capability to inhibit the growth of either human oral epidermoid carcinoma (KB) cells or human mammary epithelial (184) cells by binding to the extra-cellular domain of the human EGF receptor of the KB or 184 cells in an antigen-antibody complex.

A further object of the invention is to provide a method for inhibiting the growth of human tumor cells that express human EGF receptors and are mitogenically stimulated by human EGF comprising administering an effective amount of a monoclonal antibody to a human cancer patient having said tumor cells whereby the antibody binds to the extra-cellular domain of the human EGF receptor of the tumor cell in an antigen-antibody complex, and the monoclonal antibody being further characterized by its capability of inhibiting the growth of either 184 or KB cells.

The invention further comprises a therapeutic composition comprising a pharmaceutical carrier in association with an effective amount of either one of the novel monoclonal antibodies to inhibit the growth of human tumor cells that express human EGF receptors and are mitogenically stimulated by human EGF.

Applicant has also surprisingly discovered that the combined treatment of one of the novel monoclonal antibodies with anti-neoplastic drugs such as doxorubicin or cisplatin provides a more efficient treatment for inhibiting the growth of human cancer cells that express human EGF receptors and are mitogenically stimulated by human EGF than the use of the novel monoclonal antibody or the anti-neoplastic agent by itself. The combined treatment using applicant's novel monoclonal antibodies is advantageous because it combines two anti-cancer agents, each operating via a different mechanism of action to yield a cytotoxic response to human tumor cells. That approach could solve problems arising in the clinic, such as, on the one hand, the development of resistance to drugs, and on the other hand, a change in the antigenicity of the tumor cells that would render them unreactive with the antibody. Furthermore, applicant has also surprisingly discovered that the anti-neoplastic agent can be administered at levels substantially lower than the levels required when administering the antineoplastic agent by itself, which are toxic or sub-toxic to the patient. Anti-neoplastic agents other than doxorubicin or cisplatin such as bleomycin sulfate, carmustine, chlorambucil, and cyclophosphamide hydroxyurea may also be used with the novel monoclonal antibody. The aforementioned list is merely exemplary and is not intended to limit the scope of the invention.

Thus, a further object of this invention provides a method for inhibiting the growth of human tumor cells that express human EGF receptors and are mitogenically stimulated by human EGF comprising administering an effective amount of an anti-neoplastic agent and an effective amount of either one of the novel monoclonal antibodies to a human cancer patient having said tumor cells, whereby the antibody binds to the extra-cellular domain of the human EGF receptor of the tumor cell in an antigen-antibody complex.

A further object of this invention provides a therapeutic composition comprising an effective amount of either one of the novel monoclonal antibodies and anti-neoplastic agent to inhibit the growth of human tumor cells that express human EGF receptors and are mitogenically stimulated by human EGF in association with a pharmaceutical carrier.

BRIEF DESCRIPTION OF THE DRAWINGS

A more complete appreciation of the present invention and many of the attendant advantages thereof will be readily obtained as the invention becomes better understood by reference to the following detailed description in connection with the accompanying drawings. This description is not to be construed as specifically limiting the invention and such variations which would be within the purview of one skilled in this art are to be considered to fall within the scope of this invention.

In FIG. 10 one treatment comprising 1.8 mg 108 monoclonal antibody and 100 µg cisplatin was administered.

In FIG. 11 mice were treated intravenously a single time, 20 hours after the tumor implantation with 1.9 mg of 108 monoclonal antibody and 0.1 mg cisplatin (Abic, Ramat-Gan, Israel). Each of the substances were separately injected, PBS (●), monoclonal antibody (Δ), cisplatin (□), and monoclonal antibody+cisplatin (◆).

FIG. 5 demonstrates inhibition of 184AIN4-T colony formation by monoclonal aEGFR. Cells were grown in soft agar as described in Example VIII(B) in the presence of 20 nM aEGFR or 20 nM nonspecific antibodies and increasing concentrations of EGF. Data are mean (±SD) number of colonies greater than 60 µM.

FIG. 6 demonstrates the effects of aEGFR on MDA-468 colony formation. Cells were grown in soft agar as described in Example VIII(C) in the presence of 20 nM aEGFR or nonspecific antibody and increasing concentrations of EGF. Cells were also grown in the presence of EGF alone. Data are mean (±SD) number of colonies greater than 60 µM.

FIG. 8 shows a schematic diagram of the 108 and 96 recombinant $V_L$ and $V_H$ expression constructs. Nucleotide sequence at the 5' and 3' ends of the coding region of each of the constructs is shown, indicating the restriction endonuclease cleavage sites used to clone into pET8c(Km$^R$). The translation initiation and termination codons flanking the mature $V_H$ and $V_L$ coding regions also are shown.

FIG. 9 shows the nucleotide sequence of 108 $V_H$ cDNA. Codons 1–121 of the variable region of the heavy chain are shown. Underlined areas indicate the three complementary determining regions (CDR) of 108 $V_H$.

FIG. 10 shows the nucleotide sequence of 108 $V_L$ cDNA. Codons 1–108 of the variable region of the light chain are shown as well as five residues of the constant region. Boxed areas indicate the three complementary determining regions (CDR) of 108 $V_L$.

FIG. 11 shows the nucleotide sequence of 96 $V_H$ cDNA. Codons 1–118 of the variable region of the heavy chain are shown. Underlined areas indicate the three complementary determining regions (CDR) of 96 $V_H$.

FIG. 12 shows the nucleotide sequence of 96 $V_L$ cDNA. Codons 1–112 of the variable region of the light chain are shown as well as the first five residues of the constant region. Boxed areas indicate the three complementary determining regions (CDR) of 96 $V_L$. Lane 2: Cell lysate 4 hours after IPTG induction. Lane 3: Inclusion Bodies in 6M Guanidine HCl. Lane 4: Material prepared by gel filtration chromatography on Sephacryl S-200 in 6M Guanidine HCl and 1 mM β-mercaptoethanol.

FIGS. 14, 15 and 16 demonstrate the inhibition of mAb96 and EGF binding by the recombinant mAb 96 (rFv). FIG. 14. Positive control showing inhibition of $^{125}$I mAb96 binding by unlabelled mAb96. FIG. 15. Inhibition of $^{125}$I mAb96 binding by unpurified 96 Fv. FIG. 16. Inhibition of $^{125}$I-EGF binding by unpurified 96 Fv. For A and B, A431 cells were preincubated either with mAb 96 or with 96 rFv for 30 minutes at 4° C., and the radioligand was allowed to bind for 90 minutes at 4° C. For FIG. 16, cells were preincubated with 96 rFv for 90 minutes before the addition of radiolabelled EGF. 96 rFv was prepared as follows: 10 mg of each chain ($V_H$ and $V_L$ in 8M urea were mixed, rapidly diluted to 30 µg/ml, and then concentrated in a stirred cell apparatus. Insoluble material was discarded. Approximately 5% of the final unpurified material is correctly refolded 96 rFv.

DETAILED DESCRIPTION OF THE INVENTION

EXAMPLE I

Production of Monoclonal Antibodies

A. Immunization and Somatic Cell Hybridization

Figure 1:
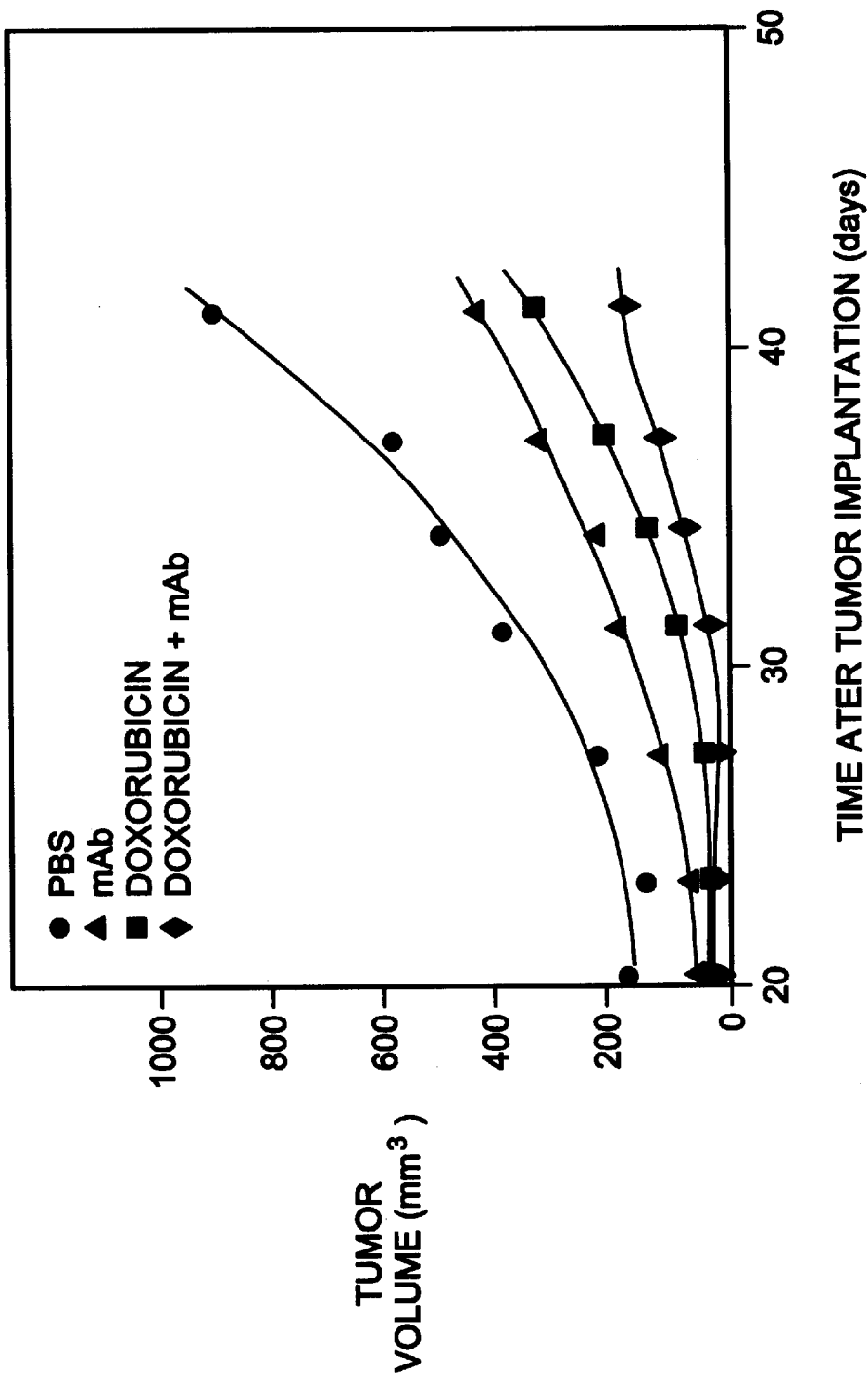
FIG. 1 demonstrates antitumor activity of 108 mAb in combination with doxorubicin against KB cells implanted subcutaneously. Four doses of 0.45 mg of 108 monoclonal antibody and 37.5 µg of adriamycin were given 24 hours after the tumor injection and repeated 3 times at 3–4 day intervals.

Balb/c mice were immunized by intraperitoneal injections of CH 71 cells or CH 71 cell membrane preparation. CH 71 cells are Chinese hamster ovary cells which have been transfected with a plasmid bearing a truncated form (deletion of most of the intracellular domain of the EGF-R) of the EGF-R cDNA (Livneh et al., *J. Biol. Chem.*, Vol. 260, 12490 (1986). These transfected cells express approximately $10^6$ mutant EGF-R molecules/cell. The choice of CH-71 cells allows the selection in the first screening test of only hybridomas secreting antibodies against the extracellular domain of the EGF-R and avoids the selection of antibodies directed against the human specific carbohydrates linked to the human EGF-R molecule.

The mice were immunized three times on day 0, 13, and 32. The two best responding mice were each boosted by three intraperitoneal injections of CH 71 cells three consecutive days before the fusion. On day 65, the spleen cells of the mice were then fused with NS1 myeloma cells (ratio 5/1) according to the general procedure of Kohler and Milstein, using PEG 4000 (Merck) as the fusing agent. (Kohler and Milstein, Eur. J. Immuno., Vol. 6, 511–519 (1976).

B. Selection and Growth of Hybridoma

The fusion product was diluted in hypoxanthineazaserine (HA) selection medium (G. Buttin et al., Current Topics In Microbiology and Immunology, Vol. 81, 27–36, (1978)) instead of the hypoxanthine-amminopterin-thymidine (HAT) selection medium and distributed in 96 well plates.

The presence of specific antibodies in the medium of the wells of the growing hybridoma cells was first assayed by radioimmunoassay. Cells expressing or not expressing the EGF receptor were plated in 96 well plates. At confluency, they were washed once with binding medium (DMEM, 20 mM Hepes, 0.2 BSA) and incubated for 90 minutes at room temperature with 100 µl of culture supernatant from the different growing hybridomas. Cells were then washed 3 times with binding medium and incubated for a further 60 minutes at room temperature with 100 µl of a solution of iodinated goat antimouse immunoglobulins (250,000 cpm/ 100 µl.). After 3 washes with PBS (phosphate buffered saline, pH 7.5), the cells were scraped from the wells and the radioactivity which was associated with their surface was counted using a gamma counter. The ability of the antibodies to bind specifically to the surface of cells expressing the EGF receptor (A 431, human fibroblasts or mouse 3T3 cells transfected with human EGF-R DNA constructs) was measured in this way and compared to their ability to bind to cells that do not express the EGF-R (a particular clone of mouse 3T3 cells). The positive hybridomas were cloned by limiting dilution and further tested by measuring their ability to immunoprecipitate $^{35}$S methionine or $^{32}$P labeled EGF-R from lysates of cell lines of different species (human, mouse, chicken). For this, goat antimouse immunoglobulins were bound to protein A Sepharose by incubation of goat antimouse antibody solution with protein A Sepharose beads for 30 minutes at room temperature. This was followed by washing 3 times with Hepes 20 mM, pH 7.4. Then the goat mouse Igs coated protein A sepharose beads were further incubated for 30 minutes at room temperature with the culture supernatant of the hybridomas, washed 3 times with HNTG buffer (Hepes 20 mM, 150 mM, NaCl, 0.1% Triton× 100, 10% Glycerol) and incubated for 1 hour at 4 degrees C. with the different cell lysates obtained by lysing cell monolayers with solubilization buffer (1% Triton×100, 150 mM NaCl, 20 mM Hepes, 1.5 mM EGTA, 1.5 mM $MgCl_2$, 10% Glycerol, Aprotinin, leupeptin and PMSF as protease inhibitors) and centrifugation of the lysate to discard the nuclear pellet. For $^{32}$p labeling, the immunoprecipitates were washed with HNTG 3 times and then incubated for 15 minutes with a $^{32}$P ATP solution (HNTG with 5 mM $MnCl_2$ and 3 µCi/sample of $^{32}$P ATP). Electrophoresis sample buffer was then added and the samples boiled for 10 min at 95 degrees C. prior to loading on a 7.5% SDS polyacrylamide gel. Monoclonal antibodies 108, 96 and 42 were all found to be specific for the human EGF-R. These antibodies were also tested for their ability to inhibit the binding of iodinated EGF to the surface of cells expressing EGF-R. These 3 antibodies inhibit the binding of EGF to its receptor, but the level of inhibition varied with 96>108>42.

EXAMPLE II

Culturing of Cell Lines

A. Culturing of Human Oral Epidermoid Carcinoma Cells (KB Cells)

The KB human tumor cell line derived from oral epidermoid carcinoma was obtained from the American Type Tissue Culture Collection. The cells were grown in Dulbecco's modified Eagle's medium supplemented with 10% fetal calf serum depleted of complement activity by incubation at 56° C. for 30 minutes and grown in glutamine, penicillin, streptomycin and sodium pyruvate, at 37° C. in 5% $CO_2$: 95% air atmosphere.

B. Culturing of Human Mammary Epithelial Cells (184 Cells) and Human Breast Cancer Cells (MDA-468 Cells)

184AIN4 and 184AIN4-T human mammary epithelial cells were provided by Martha Stampfer, Lawrence Berkeley Laboratory, Berkeley, Calif. 184AIN4 cells were maintained at 37 C. in 5% CO2 and IMEM supplemented with glutamine (0.6 mg/ml), fetal calf serum (0.5%), hydrocortisone (0.5 µg/ml), insulin (5 µg/ml) and EGF (10 ng/ml). 184AIN4-T were maintained at 37 C. in 5% CO2 in IMEM (Biofluids, Rockville, Md.) supplemented with glutamine (0.6 mg/ml), gentamicin (40 mg/ml) and 10% fetal calf serum. MDA-468 cells were cultured under the same conditions and medium as 184 AIN4-T cells.

C. Culturing of 96 IgM and 108 IgG2a Hybridoma Cell Lines

The 108 IgG2a hybridoma cell line was generated by immunizing mice with CH 71 cells expressing the EGF receptor and cultured under the same conditions as the KB cell line. The 96 IgM hybridoma cell line was generated by the same procedure as that described for the 108 IgG2a hybridoma cell line.

EXAMPLE III

A. Purification of 108 Monoclonal Antibodies from Animals

Ascites from animals injected with the 108 IgG2a hybridoma cells were clarified by centrifugation in an Eppendorf centrifuge at 4° C. for 10 min. Monoclonal antibodies were precipitated by slow addition of saturated ammonium sulfate at 4° C. to a final concentration of 45% (v/v), pH 7.5, for 24 hours. The precipitate was collected by centrifugation at 10,000 g for 15 minutes and washed twice with 50% v/v ammonium sulfate, pH 7.5. at 4° C. Further purification was carried out by affinity chromatography on Sepharose CL protein A (Pharmacia) in 0.14M Tris buffer, pH 8.0 and the 108 monoclonal antibody was eluted with 0.1M citrate buffer, pH 3.0, followed by extensive dialysis against PBS.

B. Purification of 96 Monoclonal Antibodies from Animals

Ascites from animals injected with the 96 IgM hybridoma cells were clarified by centrifugation in a low speed centrifuge at 3000 RPM for 15 minutes, at 4° C. Monoclonal antibodies were precipitated by slow addition of saturated ammonium sulfate at 4° C. to a final concentration of 45% (v/v), pH 7.5, for 24 hours. The precipitate was collected by centrifugation at 10,000 g for 15 minutes and washed twice with 50% v/v ammonium sulfate, pH 7.5 at 4° C. The precipitate was then dissolved in and dialyzed extensively against 50 mM TRIS, pH 8, 0.5 M NaCl. This material was semi-purified by gel filtration using Sephacryl S-3000 equilibrated in 50 mM TRIS, pH 7.8, NaCl 0.5 M. The peak containing the mAb96 antibody was pooled and dialyzed against PBS.

EXAMPLE IV

Purification, Specific Activity and Immunoreactivity of F (ab)$'_2$, and F(ab)' Fragment of 108 Monoclonal Antibody 108 monoclonal antibody (5 mg/ml) in 0.1M sodium-acetate buffer at pH 3.9 was digested in the presence of 4% w/w pepsin (Worthington Biochemical Corporation, New Jersey) for 7 hours at 37° C. Digestion was terminated by adjusting the pH to 8.0 with 2M Tris, followed by dialysis against PBS at 4° C. Remaining intact IgG molecules were removed by protein A affinity chromatography. The Fc portion and smaller fragments were removed by gel filtration on Sepharose G-100. For the preparation of monovalent Fab' fragment, the F(ab)$'_2$ (2 mg/ml) was reduced by 10 mM dithiothreitol in 20 mM Tris buffer, pH 8.2, for 1 hour at 37° C. Alkylation was performed in 40 mM iodoacetamide for 30 minutes at 37° C., followed by extensive dialysis against PBS at 4° C. Purity and complete digestion of the various fragments were analyzed by sodium dodecylsulfate polyacrylamide gel electrophoresis (SDS-PAGE). $^{125}$I-labeling of 108 monoclonal antibody was performed by the chloramine T method (Hunter and Greenwood, Preparation of $^{131}$Iodine Labeled Human Growth Hormone of High Specific Activity, Nature, Vol. 196, 465–6, (1962)). Specific activities of about 3×10$^6$ cpm/μg IgG were usually obtained.

The F(ab)$'_2$ and F(ab) fragments of 108 monoclonal antibody were fully immunoreactive when compared to native intact 108 monoclonal antibody in their capacity to compete with the binding of $^{125}$I labeled 108 to EGF receptors exposed on KB cells.

EXAMPLE V

108 Monoclonal Antibody Binding Properties

A. 108 Monoclonal Antibody Binding Activity to Cell Surface EGF Receptors

The antibody binding activity of 108 hybridoma supernatant was determined by an indirect immunofluorescence assay. KB cells (2×10$^6$ per sample) were trypsinized 24 hours before the assay and placed in test tubes (Falcon, polystyrene round bottom tubes). Prior to assay, the KB cell suspensions were washed with cold PBS and incubated with 108 hybridoma supernatant for 45 min. at 4° C. After washing with PBS containing 1% bovine serum albumin, the cells were incubated with fluorescein labeled rabbit anti-mouse IgG for 45 min. at 4° C. Cell samples were suspended in PBS and analyzed by a fluorescence cell sorter (FACS II, Bectin Dickenson, Mountainview, Calif. U.S.A.).

Uniformity of receptor expression was shown by positive stain in at least 96% of the cells compared with absence of staining observed with supernatant of hybridoma raised against human hepatitis B virus (7HO1). Scatchard analysis of antibody binding parameters at 4° C. revealed an average of 2×10$^5$ binding sites per cell with KD of 1.8×10$^{-9}$ M$^{-1}$.

B. A Competitive Radioimmunoassay of Epidermal Growth Factor with 108 Monoclonal Antibody and its Fragments KB cells (10$^5$/well in 24 well plates; NUNC) were grown for 24 hours, washed with PBS and incubated with different concentrations of either native antibody or its fragments in DMEM containing 1% bovine serum albumin for 1 hour at 4° C., or at room temperature, in the presence of $^{125}$I 108 monoclonal antibody (about 1×10$^6$ cpm/ml.). The cells were then washed, solubilized in 0.5N NaOH and their radioactivity was determined in a counter (Kontron, Switzerland). Non-specific binding was determined by the addition of 100-fold excess of unlabelled monoclonal antibody. Results are presented as the percentage of radioactivity associated with the cells incubated with unlabelled antibody (intact or fragmented) vs. radioactivity associated with cells incubated without the addition of cold antibody.

EGF competes with the binding of the antibody to the receptor to a maximal level of about 70%.

C. In Vivo Localization of the Radiolabeled 108 Monoclonal Antibody

KB cells (4×10$^6$) were inoculated subcutaneously on the back of nude mice (5–6 weeks old). After 14 days, when the tumor reached a size of about 1.2 cm. diameter, $^{125}$I 108 monoclonal antibody was injected intravenously or intraperitoneally (5×10$^6$ cpm; 3×10$^6$ cpm/μg). 7H01 $^{125}$I monoclonal antibody to human hepatitis B virus IgG2a served as control. Four days after the administration of antibodies, animals were killed and the radioactivity in the different tissues was determined. Means of at least four animals per group are presented.

Both intravenous and intraperitioneal administration of the tagged 108 monoclonal antibody resulted in antibody concentration at the tumor mass. Administration of control IgG resulted in no concentration at the tumor mass when given intravenously, while a marginal concentration in the tumor was detected when the antibodies were administered intraperitoneally. The percentage of injected dose accumulated at the tumor mass 96 hours post intravenal injection were 7.8±1.1 and 0.8±0.1 for monoclonal antibody 108 and 7HOI monoclonal antibody (control antibody) respectively, and for the intraperitioneal injection 7.5±0.4 and 1.8±0.2 respectively.

EXAMPLE VI

96 Monoclonal Antibody Binding Properties: A Competitive Radioimmunoassay of Epidermal Growth Factor with 96 Monoclonal Antibody Washed, confluent MDA-468 cell monolayers in 24-well culture plates were incubated at 4 C. for 2.5 hours with or without various concentrations of antibody or unlabeled EGF in binding buffer (IMEM, 0.1% BSA, 50 mM HEPES)I [$^{125}$I]EGF (S.A. 80–160 µCi/µg, ICN Radiochemicals, CA) was added for a final concentration of 1 nM. After incubation the monolayers were washed, solubilized with lysis buffer (10 mM Tris, 1 mM EDTA, 0.5% SDS, pH 7.4) and radioactivity was determined using a gamma-counter (LKB-Pharmacia).

All four antibodies were able to inhibit the binding of labeled EGF whereas nonspecific IgG or IgM were ineffective. The two antibodies most effective in inhibiting cell growth (125 IgM and 225 IgG) were also the most effective in inhibiting [$^{125}$I]EGF binding. These antibodies were able to block [$^{125}$I]EGF binding to a greater extent than unlabeled EGF.

EXAMPLE VII

Utility of 108 Monoclonal Antibody

A. Colony Inhibition Assay of KB Cells

KB cells were seeded in petri dishes (50×15 mm$^2$, NUNC) at a concentration of 2×10$^2$ cells per dish. After 16 to 24 hours medium was replaced with a fresh one containing different concentrations of either native or fragmented 108 monoclonal antibody with or without EGF. On the sixth day cultures were fed with fresh medium containing the above ingredients. On the 15th day the cultures were washed with PBS, fixed with 4% v/v formaldehyde in PBS for 15 min. and stained with hematoxylin. Number of formed colonies (25 cells) was then determined.

Exposure of KB cells to EGF (160 nM) resulted in an increase to 150% in the number of colonies counted 15 days after seeding (14 days after the beginning of the treatment) as compared to cells incubated in the absence of growth factor. In addition EGF caused an increase in the size of KB cell colonies. When a similar experiment was performed in the presence of 108 monoclonal antibody (1.6 µM) the number of cell colonies was reduced to 30% of control values. Moreover, a 100 fold excess of 108 monoclonal antibody added together with EGF given at concentration which caused a 50% increase in the colony number, reduced the number of colonies to 20% of control values. Under the same conditions, F(ab)'$_2$ fragments of 108 monoclonal antibody had no effect on the number of KB colonies. Yet when added in 100-fold excess to EGF, the F(ab)'$_2$ fragments are able to abolish the effect of EGF on the number of formed colonies (from 150% to 103%). Incubation with the same concentration of monoclonal antibody to dinitrophenyl (DNP) did not affect the number of formed colonies.

B. Antitumoral Activity of 108 Monoclonal Antibody and its Fragments in Nude Mice KB cells (2×10$^6$) were injected subcutaneously into nude mice, followed by either one or several intravenal injections of the 108 monoclonal antibody, starting one day after tumor cell injection. Tumor parameters were measured twice a week with a caliper and its volume was calculated according to the formula: Tumor volume (mm$^3$)=length×width×height. In order to validate volume measurements, correlation between tumor volume and tumor weight at the day of animal killing was assessed.

The antibody was assayed for its capacity to inhibit the growth of KB cells in nude mice. Animals received 1 mg of either 108 monoclonal antibody or control monoclonal antibody to dinitrophenyl at days 1, 5, 12 and 18 after tumor inoculation. The fragments F(ab)'$_2$ and Fab' were given at antibody equivalent doses. The 108 monoclonal antibody treated group significantly retarded tumor development and growth when compared to the group treated with control monoclonal antibody (P<0017, student-t test). The F(ab)'$_2$, was found to affect tumor growth but less efficiently than the whole antibody (P<0.05 student-t test for days 12, 17, 22, 25). Fab' fragment did not affect the tumor growth. A single 2 mg dose of 108 native monoclonal antibody given one day after injection of tumor cells was found to be as efficient as four treatments of 1 mg given at days 1, 5, 12 and 18 after tumor inoculation. In another experiment, when animals were treated with a single dose of 0.66 mg F(ab)'$_2$ fragments, the antitumoral effect was slightly lower, yet a significant difference between the control and the treated group was found using the Mann Whitney analysis (P<0.03 for days 9, 12, 14, 17) and student-t test (P<0.05 days 9, 12). At the day of sacrifice, tumors were measured and then removed for weight determination. The correlation coefficient between the tumor volume and the tumor weight was 0.95 (P<0.0001).

C. Tumor Growth in the Peritoneal Cavity

The injection of 3×10$^6$ KB cells intraperitoneally one week after mice (Nude in general background) received x-irradiation (400 rads), brought about the development of an ascitic growth. The intraperitoneal tumor-bearing mice died after 30 days. Three intravenous injections of 108 monoclonal antibody (0.5 mg each) prolonged the life span of animals with 30% of animals not developing tumors at all.

D. Tumor Growth in a Metastatic Form

The metastatic form of the KB tumor could be obtained by the injection of the cells intravenously (iv). Mice injected with, 1.5×10$^6$ KB cells developed tumor nodules in the lungs 4–6 weeks after their implantation. This tumor model mimics the situation in the clinic, where tumor cells infiltrate into internal organs. This is the major problem in the treatment of cancer. The KB cell injection was followed by 3 intravenous injections of 0.5 mg 108 monoclonal antibody at days 6, 9 and 13 after the tumor cell injection. At the termination of the experiment, the lungs were removed, fixed in formaldehyde, and paraffin embedded. Serial sections were cut 4–5 µm in thickness and stained with hematoxylin. The number of metastatic nodules of various depths through the lungs was obtained by light microscopy analysis. Isolation of three metastatic cell clones from lungs of tumor bearing animals and their assay for receptor levels revealed persistence of receptor expression. Treatment by the antibody reduced the number of lung tumor nodules to 15% of those in the respective controls. (P<0.05 Mann-Whitney analysis).

EXAMPLE VIII

Utility of 96 Monoclonal Antibody

A. 96 Inhibits 184A1N4 and MDA-468 Cell Growth

184AIN4 and MDA-468 cells were passed (5,000/well) into triplicate wells of 24-well plates and allowed to attach before antibody was added. 184AIN4 growth media contained 1 ng/ml EGF and differing amounts of EGFR antibody which was added to the growth media simultaneously with the EGF. MDA 468 growth media contained no EGF. Growth media was changed after 48 hours and the cells were counted after 4 days. At the end of the experimental growth period cells were harvested with trypsin-EDTA and counted using a Particle Data cell counter (Particle Data, Inc., Elmhurst, Ill.). Data is % control cell numbers (mean±SD). 96 IgM(●—●), 42 IgM(○—○), nonspecific IgM(Δ—Δ), 225 IgG(□—□), 108 IgG(□—□), non-specific IgG (Δ—Δ). (See FIGS. 4A–4D)

B. 96 Colony Inhibition Assay of 184AIN4 Cells

Figure 5B:
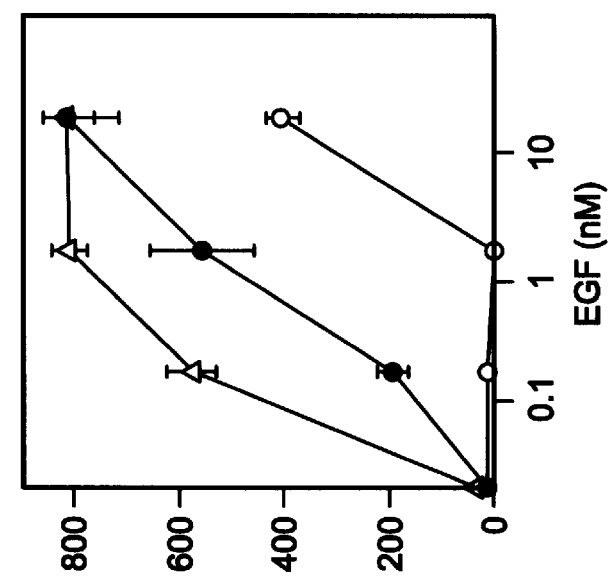
FIG. 5B) IgM: 96 IgM (○—○), 42 IgM(●—●), nonspecific IgM(Δ—Δ).
Figure 5A:
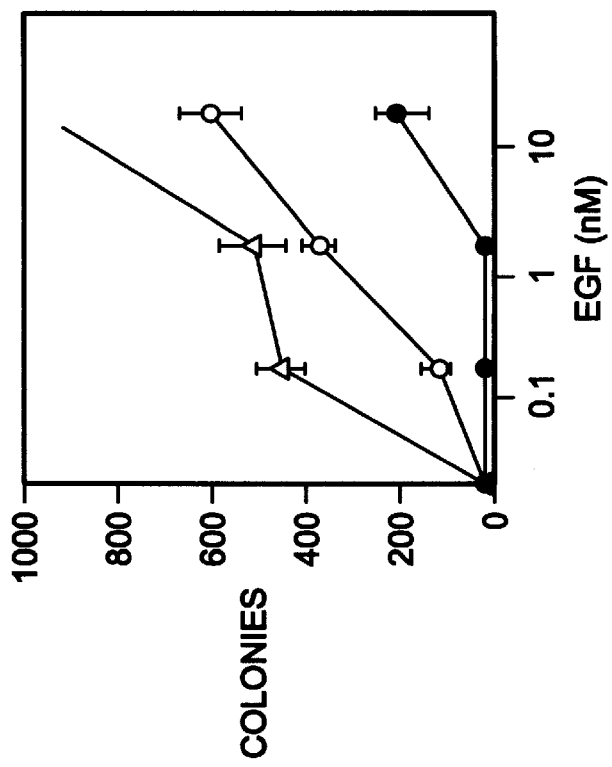
FIG. 5A). IgG:225 IgG(●—●), 108 IgG(○—○), non-specific IgG(Δ—Δ).

184AIN4-T cells were suspended in semisolid agar medium containing 0.4% Bacto-Agar (Difco, Detroit, Mich.), IMEM,10% FBS and treatments. Cells were plated (10,000/dish) into triplicate 35 nM culture dishes containing 1 ml IMEM, 0.6% agar and 10% FBS. The dishes were incubated for 10–14 days at 37 C. in 5% CO in the presence of 20 nM aEGFR or 20 nM nonspecific antibodies and increasing concentrations of EGF. Data are mean (±SD) number of colonies greater than 60 $\mu$M. A) IgG:225 IgG (●—●), 108 IgG (○—○), non specific IgG (Δ—Δ). B) IgM: 96 IgM (○—○), 42 IgM (●—●), nonspecific IgM (Δ—Δ). Cell colonies larger than 60 um in diameter were counted using a Bausch & Lomb colony counter (See FIGS. 5A–5B).

C. 96 Colony Inhibition Assay of MDA-468 Cells

Figure 6B:
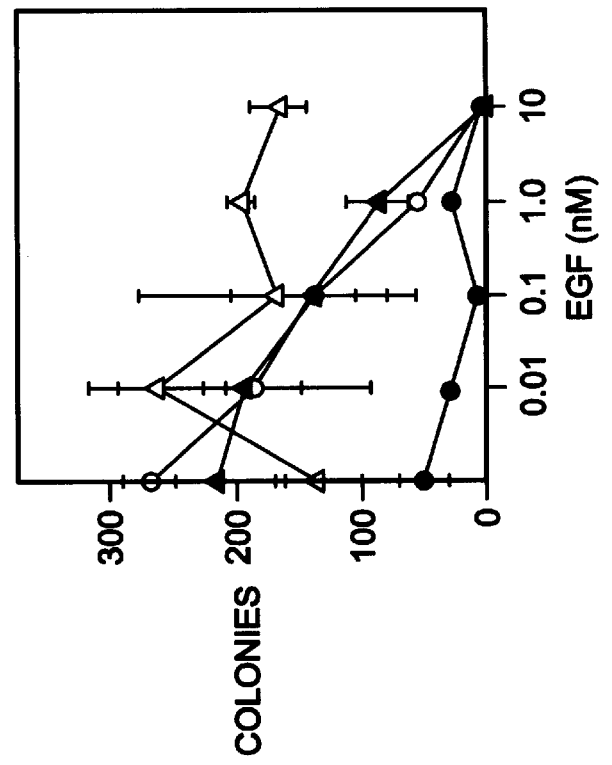
FIG. 6B) IgM: 96 IgM(Δ—Δ), 42 IgM(●—574 ), nonspecific IgM(Δ—Δ), EGF alone(○—○).
Figure 6A:
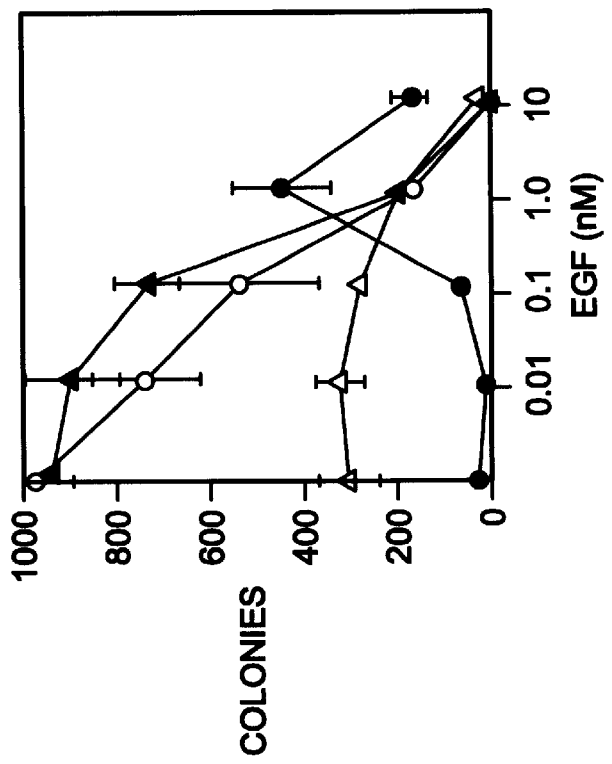
FIG. 6A) IgG: 225 IgG(●—●), 108 IgG(Δ—Δ), non-specific IgG(Δ—Δ), EGF alone (○—○).
Figure 7:
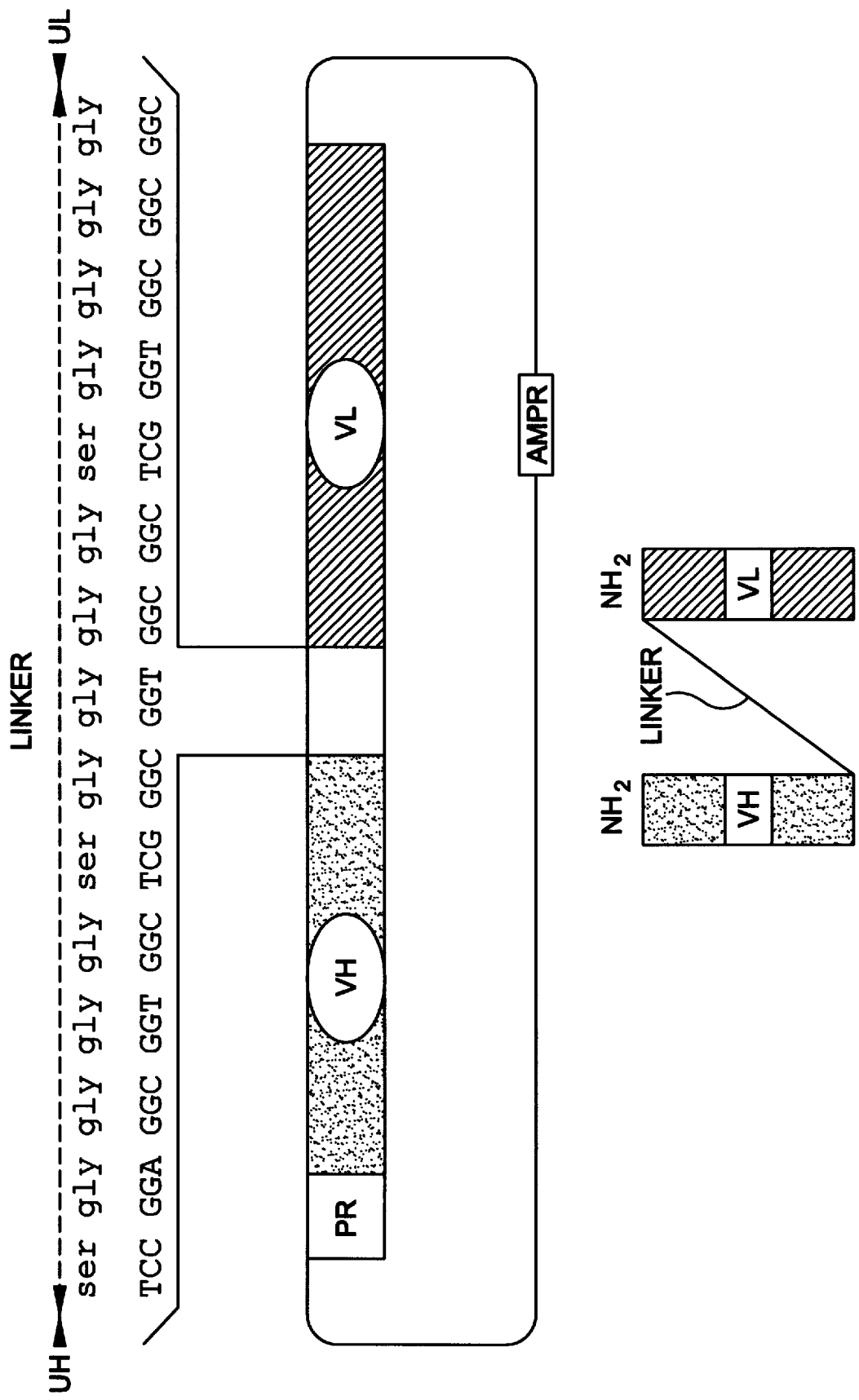
FIG. 7 shows a schematic representation of the plasmid DNA and the expressed gene product for a single-chain Fv (sFv) antibody fragment produced in E. coli. A standard PBR322 derivative plasmid with an antibiotic resistance gene (amp$^r$) contains a generic promoter with accompanying ribosomal binding site (PR). The sFv gene construct is joined to the PR region by a translation initiation codon placed immediately upstream of the native $V_H$ coding sequence. The expressed sFv gene produces a single polypeptide chain in which the carboxyl terminus of the $V_H$ domain is joined to the amino terminus of the $V_L$ domain through a 15 amino acid linker. This linker, as shown in the construct, consists of a (Gly4, Ser)3 repeat sequence (15).

MDA-468 cells were suspended in semisolid agar medium containing 0.4% Bacto-Agar (Difco, Detroit, Mich.) IMEM, 10% FBS and treatments. Cells were plated (10,000/dish) into triplicate 35 mm culture dishes containing 1 ml IMEM, 0.6% agar and 10% FBS. The dishes were incubated for 10–14 days at 37 C. in 5% C02 in the presence of 20 nM aEGFR or 20 nM nonspecific antibodies and increasing concentrations of EGF. Data are mean (±SD) number of colonies greater than 60 um. A) IgG:225 IgG (●—●) 108 IgG (Δ—Δ) non-specific IgG (Δ—Δ), EGF alone (○—○). B) IgM: 96 IgM (Δ—Δ), 42 IgM(●—●) nonspecific IgM (Δ—Δ) EGF alone (○—○). Cell colonies larger than 60 nM in diameter were counted using a Bausch & Lomb colony counter. (See FIGS. 6A–6B)

EXAMPLE IX

Utility of 108 Monoclonal Antibody

A. Administered with Doxorubicin

Monoclonal antibody 108 were injected to form a subcutaneous tumor. Four doses of 0.45 mg of 108 monoclonal antibody and 37.5 $\mu$g of doxorubicin (adriamycin) were given 24 hours after the tumor injection and repeated 3 times at 3–4 day intervals. The volume of the tumor was compared to the controls: phosphate buffered saline antibody alone or drug alone. (See FIG. 1.)

Figure 2:
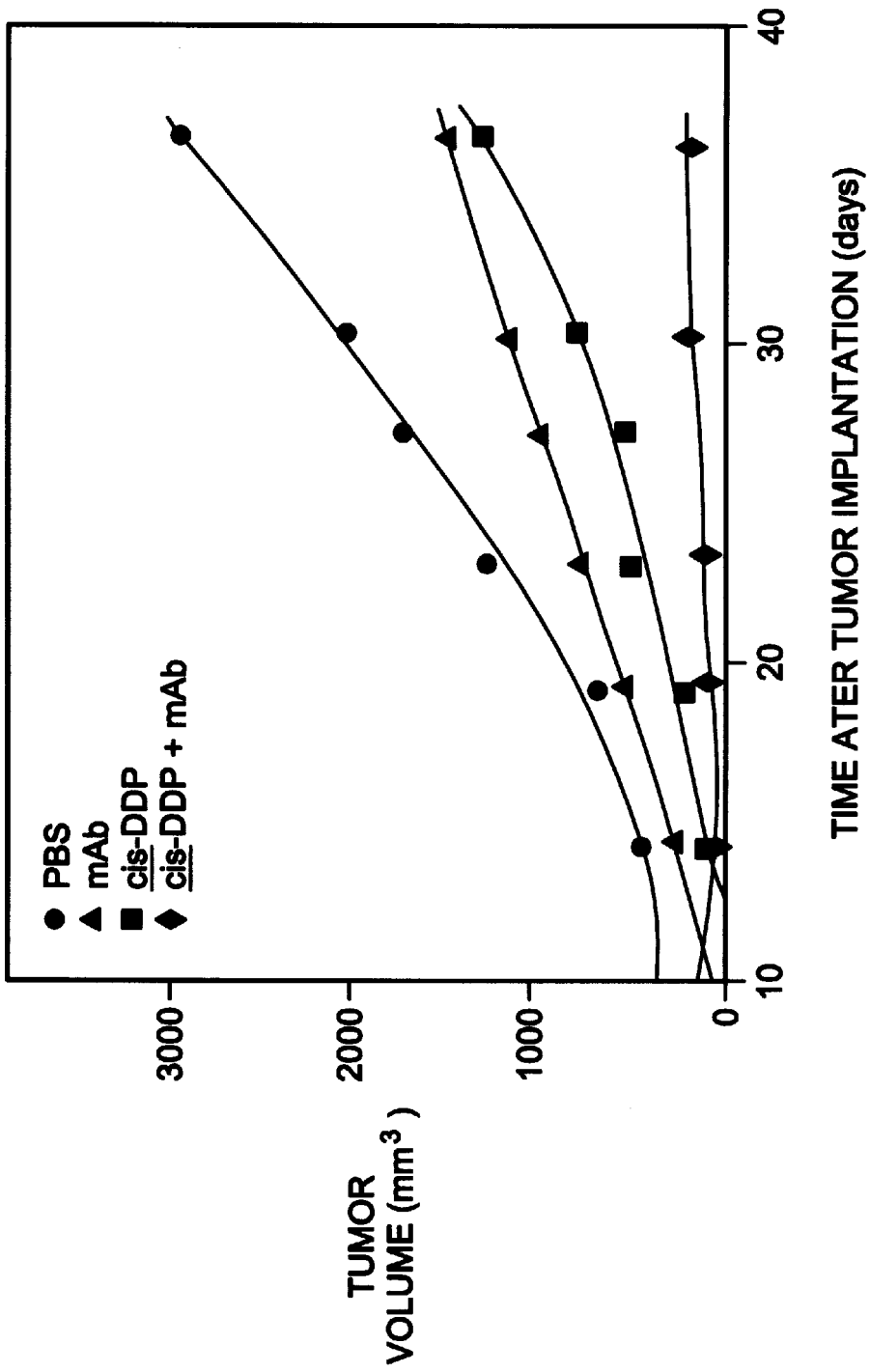
FIG. 2 demonstrates antitumor activity of 108 mAb in combination with cisplatin against KB cells implanted subcutaneously.
Figure 3:
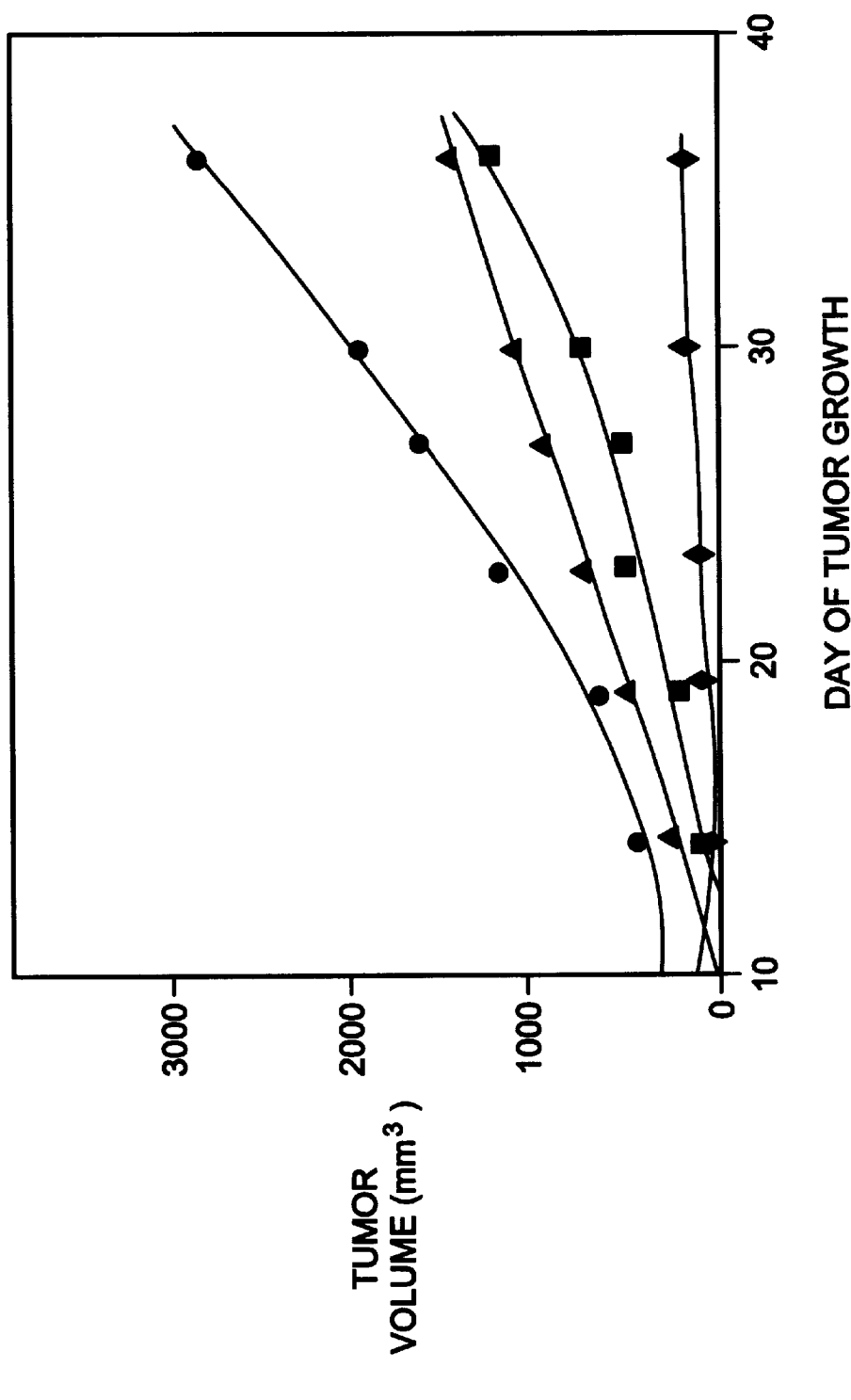
FIG. 3 demonstrates antitumor activity of 108 mAb in combination with cisplatin against KB cells implanted subcutaneously.
Figure 4A:
FIG. 4 demonstrates aEGFR inhibition of anchorage dependent cell growth. 184AIN4 (FIG. 4A and FIG. 4B) and MDA-468 (FIG. 4C and FIG. 4D) cells were passed (5,000/well) into triplicate wells of 24-well plates and allowed to attach before antibody was added. 184AIN4 growth media contained 1 ng/ml EGF. Growth media was changed after 48 hours and the cells were counted after 4 days. Data is % control cell numbers (mean±SD). 96 IgM(●—●), 42 IgM (○—○), nonspecific IgM(Δ—Δ), 225 IgG(□—□), 108 IgG (□—□), non-specific IgG(Δ—Δ).
Figure 4B:
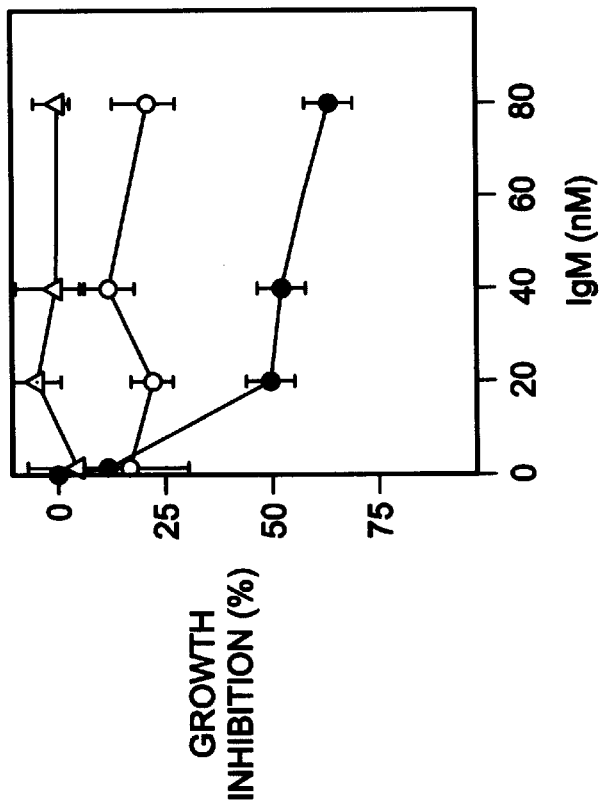
Figure 4D:
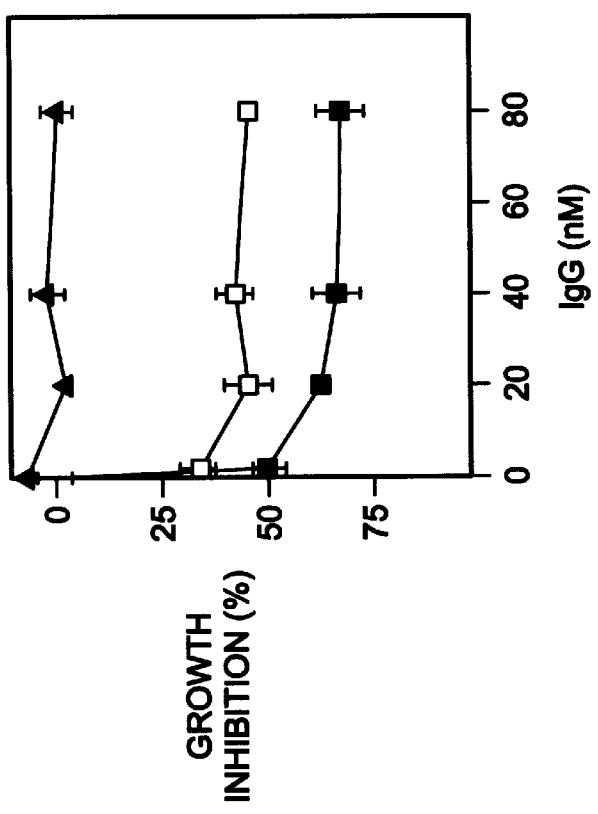
Figure 4C:
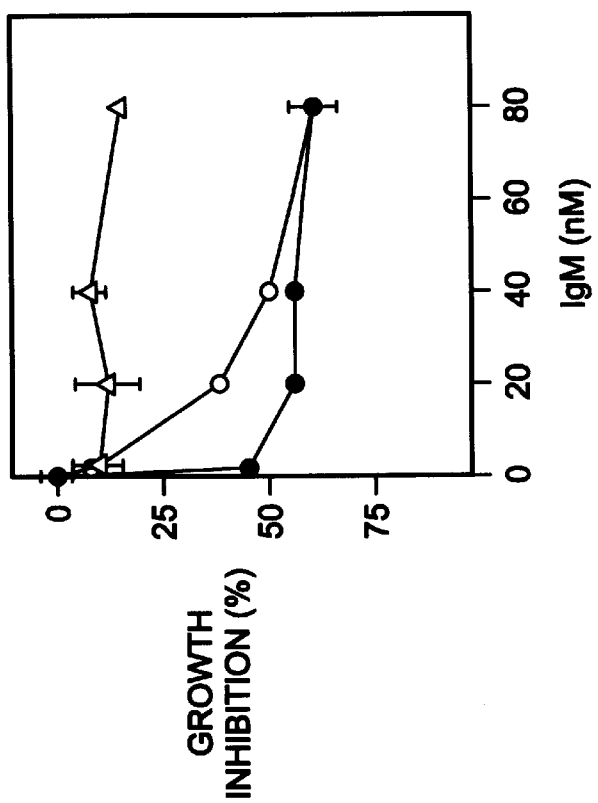

B. Administered with Cisplatin a) A single treatment comprising 1.8 mg 108 monoclonal antibody and 100 $\mu$g cisplatin was administered twenty four hours after the subcutaneous tumor inoculation with 2×10⁶ KB cells. The results are presented in FIG. 2.

b) A single treatment comprising 1.9 mg 108 monoclonal antibody and 0.1 $\mu$g cisplatin were injected intravenously each in a separate needle 20 hours after the tumor transplantation. The combined treatment was significantly better than each of the treatments alone (P<0.02 by student-t-test, P<0.007 by Mann Whitney analysis, FIG. 3).

EXAMPLE X

Expression and Recombination of Separate Chain Constructs of 96 and 108 $V_L$ and $V_H$ Chains

A. E. coli Strains and Plasmids

E. coli strain BL21 (DE3) and the plasmid expression vector pET8c were kindly provided by Dr. F. W. Studier of Brookhaven National Laboratories. This plasmid contains a fragment of T7 DNA specifying the gene 10 promoter inserted into the BamHI site of pBR322 so as to direct transcription counterclockwise. This plasmid also provides a transcription terminator for T7 RNA polymerase, a ribosome binding site and an ATG for translation initiation, with the ATG overlapping an NcoI restriction site (CCATGG).

The plasmid pET8c ($Km^R$)was also received from Dr. Studier and was constructed by removing the ampicillin resistance gene from pET-8c [21, 22, 27] via excision of a BspHI-EcoRI fragment (pBR322 bp 3195–4361) and replacing it with an 869 bp fragment encoding kanamycin resistance ($Km^R$), with the $Km^R$ gene oriented clockwise in the vector. The $Km^R$ gene derives from Tn903 [28] and was obtained using the polymerase chain reaction with pUC4KISS [29] as template. The fragment carrying the $Km^R$ gene starts 50 nucleotides ahead of the $Km^R$ initiation codon and ends exactly at the termination codon. A Stratagene pBS plasmid DNA (Bluescript II SK+, Stratagene; La Jolla, Calif.) was used as a sub-cloning vector and transformed into commercially available E. coli host cell strains such as Invitrogen DH-1 competent cells (Invitrogen, San Diego, Calif.).

B. Oligonucleotides and Chemicals

Oligonucleotides were synthesized on an Applied Biosystems Model 380A synthesizer using the phosphoramidite method. All routine chemicals (e.g. urea, Tris buffer, DNP-lysine etc.) were purchased from standard suppliers such as Sigma (St. Louis, Mo.) and Fisher (Pittsburgh, Pa.). Radioactive chemicals were purchased from New England Nuclear (Boston, Mass.). Restriction and other DNA-modifying enzymes (e.g. T4 DNA ligase, T4 polynucleotide kinase, calf intestinal phosphatase etc.) were purchased from standard biotechnology manufacturers such as New England Biolabs (Beverly, Mass.) and Boehringer Mannheim (Indianapolis, Ind.).

C. Identification of Monoclonal Antibody 108 and 96 cDNA Clones

In order to obtain cDNA clones for both 108 and 96 light and heavy chains, poly (A)-containing RNA was isolated from the respective hybridoma cell lines using standard methods [30]. The first strand cDNA was synthesized using an oligo (dT) primer. The first strand cDNA was then used as a template for second strand synthesis using the method of Gubler and Hoffman [31]. The double stranded cDNA was then treated with EcoRI methylase and DNA polymerase using reaction conditions described in Maniatis [30]. The mixture was then cleaved with EcoRI and fractionated on an 8% polyacrylamide gel. DNA with a size greater than 600 bp was eluted from the gel and then collected by ethanol precipitation. The cDNA was then inserted into EcoRI cleaved and phosphatase treated lambda gt11 DNA using T4

DNA Ligase, to produce a library of approximately one million transformants. Two separate libraries were constructed, one for identifying 108 sequences and the second for identifying 96 sequences. $V_H$ and $V_L$ cDNA clones were identified by hybridization with an oligonucleotide probe specific for the constant region. Insert DNA from positive phage was subcloned into pBS vectors. The DNA sequence for the $V_H$ and $V_L$ coding regions were verified for all $V_H$ and $V_L$ clones selected for further study. DNA sequencing reactions were carried out as per manufacturers instructions (Sequenase, USB; Cleveland, Ohio).

cDNA clones encoding the variable regions of both monoclonal antibody 96 and 108 heavy and light chains were obtained from cDNA libraries constructed from the respective hybridoma cell lines. The nucleotide sequence of all four variable regions is shown in FIGS. 9–12.

D. Construction of Expression Vectors for $V_H$ and $V_L$ cDNA

In order to direct expression of the various $V_H$ and $V_L$ cDNAs they were placed under the control of the bacteriophage T7 promoter[21, 22, 27]. In this system, the cDNA is placed into a vector containing the promoter and translation initiation signals for the TØ protein of bacteriophage T7. T7 RNA polymerase can then be delivered to the host cell by either induction or infection. In the present example the antibody expression vectors were placed into a cell that carries a prophage containing the gene for T7 RNA polymerase under control of the lac UV5 promoter. Addition of the lactose analog IPTG to a growing culture of cells induces T7 RNA polymerase, which in turn transcribes the target DNA in the plasmid. Transcription by T7 RNA polymerase is so active that target RNA can accumulate to amounts comparable to ribosomal RNA and target proteins can constitute the majority of cellular protein.

Plasmids expressing the antibody $V_L$ or $V_H$ sequence and conferring resistance to kanamycin were constructed from pET-8c(Km$^R$) and PCR products derived from the various cDNAs. Briefly, four oligonucleotides each capable of hybridizing to the 5' of one of the various cDNAs were designed. All four oligonucleotides incorporated an NcoI restriction site. Similarly, four oligonucleotides each capable of hybridizing to the 3' of one of the various cDNAs were also designed. In the latter case all four oligonucleotides incorporated an BamHI restriction site.

Four separate PCR reactions were carried out using the appropriate combination of template DNA (108 $V_H$ or $V_L$ and 96 $V_H$ or $V_L$) and PCR primers. Following 30 cycles of PCR the various reaction products were digested with NcoI and BamHI and the insert fragment was then ligated to NcoI/BamHI cleaved pET8c(Km$^R$). The resulting plasmid DNA was then transformed into *E. coli* DH-1 cells and a single isolate from each transformation was identified that released the appropriate size fragment by digestion with NcoI and BamHI. DNA from a positive isolate for each of the four chains was then used to transform *E. coli* BL21 (DE3). A single isolate from each of these transformations was the used for expression of the various chains as described below. A schematic diagram of the expression vector constructs is indicated in FIG. 8.

E. Expression of $V_H$, $V_L$, and sFv Genes in *E. coli*

Fresh overnight cultures were diluted 1:100 and grown to an O.D.595 of ~0.4 and then induced with 1 mM isopropyl β-D-thiogalactopyranoside (IPTG). Samples were removed at selected time points, centrifuged and the pellet resuspended in sample buffer (20 mM Tris-HCl pH 6.8, 3.0% SDS, 15% glycerol, 0.1-β-mercaptoethanol, 0.001% bromophenol blue dye) before analysis by SDS gel electrophoresis [32].

Expression vectors containing the various recombinant Fv constructs under the control of the T7 promoter were introduced into BL21 (DE3) cells [21, 22, 27]. This cell line is an *E. coli* lysogen containing a single copy of the gene for T7 RNA polymerase in the chromosome under the control of the IPTG-inducible lac UV-5 promoter. The addition of IPTG to cell cultures elevates the expression levels of T7 RNA polymerase and thus indirectly induces the expression of recombinant proteins under the control of T7 promoters.

F. Protein Purification

The first step in the purification of the individual $V_H$, $V_L$, or sFv proteins was their isolation in the form of bacterial inclusion bodies. *E. coli* cell pellets from 500 ml induced cultures (2–4 hours with 1 mM IPTG) were resuspended in 20 ml of 50 mM Tris-HCl, pH 9.0, 2.0% glycerol and 0.1 mM EDTA. This suspension was sonicated 2×15 sec. on ice and then centrifuged at 15,000 g for 20 min. The precipitate (containing essentially all of the $V_H$, $V_L$, or sFv proteins) was resuspended in 8 M urea, 50 mM Tris-HCl pH 8.0, sonicated 2×15 sec. on ice, stored overnight at 4° C. and then clarified by centrifugation at 15,000 g for 20 min. Supernatant samples in urea were adjusted to ~1 mg/ml (VH, VL) or ~0.1 mg/ml (sFv), as calculated from absorbance measurements using extinction coefficients $E_{280\ nm\ 1\ cm}^{0.1\%}$=2.0 for $V_H$, 1.0 for $V_L$, or 1.5 for Fv (used also to estimate sFv) [6] and stored overnight at 4° C. These samples were either used directly for analysis of refolding and recovery of active Fv or processed for further purification.

$V_H$, $V_L$, and sFv proteins purified from bacterial inclusion bodies were solubilized in 6 M Guanidine HCl, 50 mM Tris-HCl pH 8.0, 5 mM EDTA and 1 mM β-mercaptoethanol. Size exclusion chromatography was performed on a Sephacryl S-200 column (3×90 cm). Samples of S-200 purified $V_H$, $V_L$, or sFv protein were further treated by ion-exchange chromatography following buffer exchange by dialysis to 8 M urea, 50 mM Tris-HCl pH 8.0, 20 mM NaCl, 0.01 mM β-mercaptoethanol. Samples were passed over a 5 ml Q-Sepharose anion exchange column and eluted with a 0.02–0.5 M NaCl gradient in 8 M Urea, 50 mM Tris-HCl pH 8.0.

Peptides from each of the separate chain constructs ($V_H$ or $V_L$) and the sFv were found primarily in the form of insoluble inclusion bodies. This finding was consistent for proteins over-expressed in *E. coli* [34] and from a purification standpoint, this sequestration was useful since recombinant proteins were conveniently isolated in a highly enriched form.

$V_H$, $V_L$, and sFv proteins exhibited minimal solubility in nondenaturing solvents and, therefore, were dissolved in either 8 M urea or 6 M guanidine hydrochloride (Guanidine HCl). When these chaotropes were removed either slowly by dialysis or rapidly by dilution, $V_L$ remained soluble longer than $V_H$. However, neither individual chain remained in solution in PBS except at low protein concentration (less than 50 μg/ml). Significantly recombinant $V_H$ and $V_L$ chains did remain in solution in PBS at concentrations up to ~1 mg/ml when later recovered as active Fvs.

Further purification of recombinant $V_H$, $V_L$, or sFv proteins isolated in inclusion bodies and solubilized in Guanidine HCl with reduction was performed by size exclusion chromatography. Recoveries of S-200 purified $V_H$, $V_L$, and sFv proteins following size exclusion chromatography varied with different inclusion body preparations and ranged from 100–200 mg/liter.

G. Refolding of $V_H$, $V_L$, and sFv Peptides

The refolding of $V_H$ and $V_L$ peptides was carried out by the method of Hochman et al.[18, 33] Equimolar amounts of $V_H$ and $V_L$ proteins were added together in 8 M urea, 50 mM Tris-HCl, pH 8.0, to a final protein concentration of ~1 mg/ml. Refolding was initiated by the removal of chaotrope either by extensive dialysis in PBS or by rapid dilution 20-fold into PBS. Refolded material following rapid dilution (final urea concentration equal to 0.4 M) was maintained at room temperature for a minimum of 30 minutes.

Refolding of sFv protein was preceded by reduction of sFv in 8 M urea, 50 mM Tris-HCl, pH 8.0, at 37° C. for 1 hour with 0.1 M β-mercaptoethanol. Reduction was carried out at protein concentrations of 1 mg/ml and then diluted with the same buffer to 50–100 μg/ml. The diluted sample was then dialyzed extensively, first against 8 M urea, 50 mM Tris-HCl, pH 8.0, and then to final equilibration in PBS.

Recombinant $V_H$ and $V_L$ and sFv peptides expressed to high levels in *E. coli* were found to be, as anticipated, sequestered in insoluble inclusion bodies. As a result, strong denaturants were required for protein solubilization. The recovery of active protein following this treatment was dependent upon the use of an effective in vitro refolding procedure.

Figure 13:
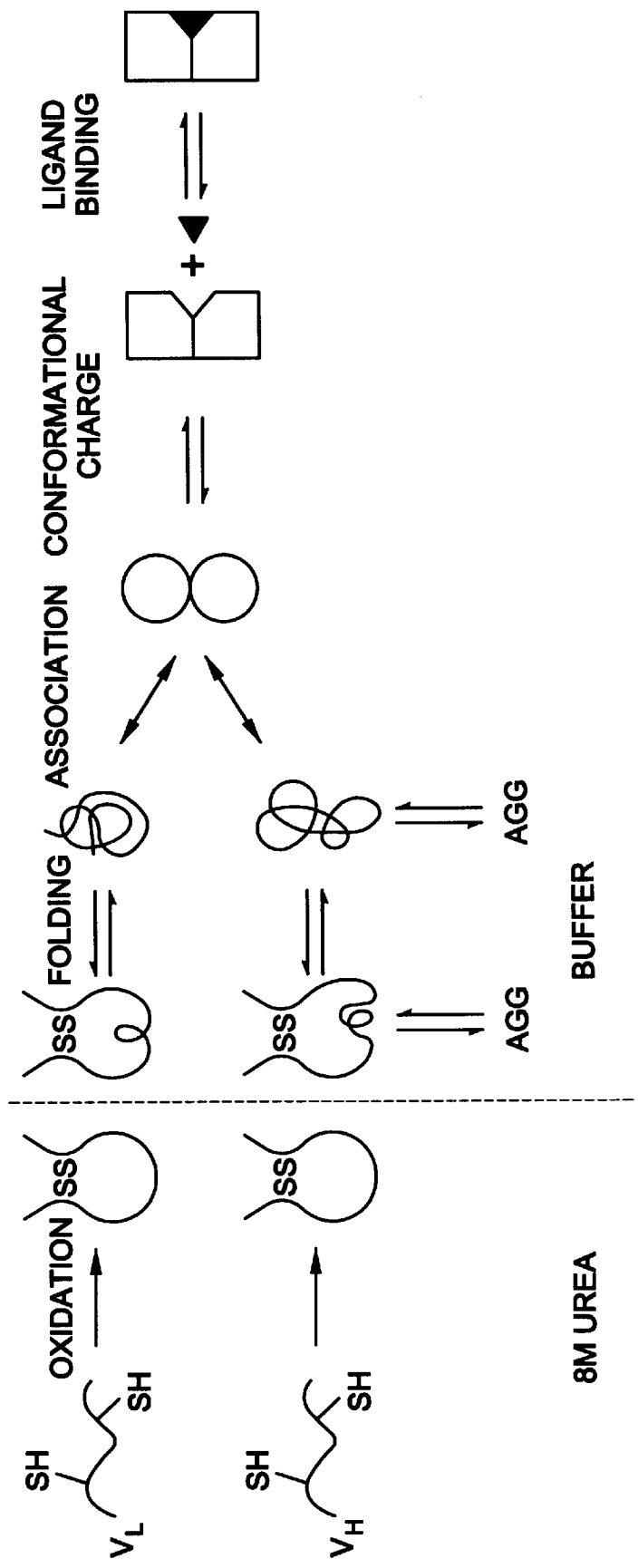
FIG. 13 shows a schematic representation of the renaturation of antibody Fv from denaturant. Starting from the left of the diagram, oxidation of the individual $V_H$ and $V_L$ chains takes place in the presence of denaturant. Refolding takes place following the removal of chaotrope and its replacement with PBS (buffer). Properly refolded $V_H$ and $V_L$ chains reassociate to form an active Fv complex capable of binding ligand. Incorrectly refolded chains form increasingly insoluble aggregates (agg).

In general, protein refolding is initiated by the removal of the solubilizing chaotrope under conditions designed to promote the most effective outcome. FIG. 13 illustrates this general scheme by outlining a simple model of the steps required for protein refolding of an antibody Fv. In this model, oxidation of the individual $V_H$ and $V_L$ chains takes place separately, each in the presence of denaturant. Intrachain disulfide bond formation within the relaxed chains is concentration dependent and the proper formation of these bonds presumably promotes the most effective subsequent refolding. Refolding itself is initiated by the transfer of the combined $V_H$ and $V_L$ protein from denaturant into a physiological buffer (e.g. PBS). Successfully refolded $V_H$ and $V_L$ chains can then associate together to form an active Fv complex capable of specific ligand binding.

A standard procedure for the refolding of recombinant 108 and 96 $V_L$ and $V_H$ was adopted based upon the conditions originally used by Hochman et al. [18, 33] to renature the native MOPC315 $V_H$ and $V_L$. Solubilized recombinant 108 or 96 $V_H$ and $V_L$ chains (either directly from inclusion bodies or after further purification) were allowed to oxidize in air to greater than 90%. The separate chains were combined in denaturant, diluted 1:20 in PBS, and allowed to refold at room temperature. The refolded chains were then used in the binding experiments described below.

H. Biological Activity

FIGS. 14 and 15 show that in a competition binding experiment, the 96 rFv competed for binding of MAb 96 to A431 cells. Similar results were observed for 108 rFv competing for MAb 108 binding to A431 cells. The 96 rFv also inhibited the binding of radioiodinated EGF to A431 cells, as shown in FIG. 16.

Antibody fragments may be produced by proteolytic degradation of entire immunoglobulin molecules, or by recombinant expression of DNAs encoding antibody fragments. The antibody fragment 96 Fv does not cause the receptor to dimerize, and does not activate the receptor. The antibody fragment induces internalization of the receptor without inducing its degradation. A toxin, radiochemical, or drug can be attached to the antibody fragment. The use of a variable region antibody fragment directed to a cellular receptor is useful in targeting drug delivery to cells expressing that receptor in order to affect cellular physiology and/or metabolism.

References

1. Roitt, I. M., J. Brosstoff, and D. K. Male, *Immunology*. 1985, London: Gower Medical Publishing.
2. Cabilly, S., A. D. Riggs, and H. Pande et al., Generation of antibody activity from mmunoglobulin polypeptide chains produced in *Escherichia coli*. Proc. Natl. Acad. Sci. USA., 1984. 81: p. 3273–3277.
3. Boss, M. A., et al., Assembly of functional antibodies from immunoglobulin heavy and light chains synthesised in *E coli*. Nucl. Acids. Res., 1984. 12: p. 3791–3806.
4. Inbar, D., J. Hochman, and D. Givol, Localization of antibody-combining sites within the variable portions of heavy and light chains. Proc. Natl. Acad. Sci. USA., 1972. 69: p. 2659–2662.
5. Hochman, J., et al., Folding and interaction of subunits at the antibody combining site. Biochemistry, 1976. 15: p. 2706–2710.
6. Hochman, J., D. Inbar, and D. Givol, An active antibody fragment (Fv) composed of the variable portions of heavy and light chains. Biochemistry, 1973. 12: p. 1130–1135.
7. Skerra, A. and A. Plückthun, Assembly of a functional immunoglobulin FV fragment in *Escherichia coli*. Science, 1988. 240: p. 1038–1041.
8. Better, M., et al., *Escherichia coli* secretion of an active chimeric antibody fragment. Science, 1988. 240: p. 1041–1043.
9. Plückthun, A., et al., Engineering of antibodies with a known three-dimensional structure. Cold Spring Harbor Symp. Quant. Biol., 1987. LII: p. 105–112.
10. Horwitz, A. H., et al., Secretion of functional antibody and Fab fragment from yeast cells. Proc. Natl. Acad. Sci. USA., 1988. 85: p. 8678–8682.
11. Huse, W. D., L. Sastry, and S. A. Iverson et al., Generation of a large combinatorial library of the immunoglobulin repertoire in phage lambda. Science, 1989. 246: p. 1275–1281.
12. Mullinax, R. L., E. A. Gross, and J. R. Amberg et al., Identification of human antibody fragment clones specific for tetanus toxoid in a bacteriophage lambda immunoexpression library. Proc. Natl. Acad. Sci. USA., 1990. 87: p. 8095–8099.
13. Caton, A. J. and H. Koprowski, Influenza virus hemagglutinin-specific antibodies isolated from a combinatorial expression library are closely related to the immune response of the donor. Proc. Nati. Acad. Sci. USA., 1990. 87: p. 6450–6454.
14. Winter, G. and C. Milstein, Man-made antibodies. Nature, 1991. 349: p. 293–299.
15. Huston, J. S., D. Levinson, and M. Mudgett-Hunter et al., Protein engineering of antibody binding sites: recovery of specific activity in an anti-digoxin single-chain Fv analogue produced in *Escherichia coli*. Proc. Natl. Acad. Sci. USA., 1988. 85: p. 5879–5883.
16. Bird, R. E., K. D. Hardman, and J. W. Jacobson et al., Single-chain antigen-binding proteins. Science, 1988. 242: p. 423–426.
17. Tai, M.-S., M. Mudgett-Hunter, and D. Levinson et al., A bifunctional fusion protein containing Fc-binding fragment B of staphylococcal protein A amino terminal to antidigoxin single-chain Fv. Biochemistry, 1990. 29: p. 8024–8030.

18. Chaudhary, V. K., et al., A recombinant single-chain immunotoxin composed of anti-Tac variable regions and a truncated diphtheria toxin. Proc. Natl. Acad. Sci. USA., 1990. 87: p. 9491–9494.
19. Batra, J. K., et al., Single-chain immunotoxins directed at the human transferrin receptor containing Pseudomonas exotoxin A or diptheria toxin: anti-TFR(Fv)-Pe40 and DT388-anti-TFR (Fv). Mol. Cell. Biol., 1991. 11: p. 2200–2205.
20. Chovnick, A., et al., A recombinant, membrane-acting immunotoxin. Cancer Res., 1991. 51: p. 465–467.
21. Studier, F. W., et al., Use of T7 RNA Polymerase to Direct Expression of Cloned Genes. Methods in Enzymology, 1990. 185: p. 60–89.
22. Studier, F. W. and B. A. Moffat, Use of bacteriophage T7 RNA polymerase to direct selective high-level expression of cloned genes. J. Mol. Biol., 1986. 189: p. 113–130.
23. Condra, J. H., V. V. Sardana, and J. E. Tomassini et al., Bacterial expression of antibody fragments that block human rhinovirus infection of cultured cells. J. Biol. Chem., 1990. 265: p. 2292–2295.
24. Field, H., G. T. Yarranton, and A. R. Rees, Expression of mouse immunoglobulin light and heavy chain variable regions in *Escherichia coli* and reconstitution of antigen-binding activity. Protein Engineering, 1989. 3: p. 641–647.
25. Baldwin, E. and P. G. Schultz, Generation of a catalytic antibody by site-directed mutagenesis. Science, 1989. 245: p. 1104–1107.
26. Cheadle, C., et al., Cloning and expression of the variable regions of mouse myeloma protein MOPC315 in *E. coli:* Recovery of active Fv fragments. Molecular Immunology, 1992. 29(1): p. 21–30.
27. Rosenberg, A. H., et al., Vectors for selective expression of cloned DNA's by T7 RNA polymerase. Gene, 1987. 56: p. 125–135.
28. Oka, A., H. Sugisaki, and M. Takanami, Nucleotide sequence of the kanamycin resistance transposon Tn903. The Journal of Molecular Biology, 1981. 147: p. 217–226.
29. Barany, F., Single-stranded hexameric linkers: A system for in-phase insertion mutagenesis and protein engineering. Gene, 1985. 37: p. 111–123.
30. Maniatis, T., E. F. Fritsch, and J. Sambrook, Molecular Cloning: A Laboratory Manual. 1982,.
31. Gubler, U. and B. J. Hoffman, A simple and very efficient method for generating cDNA libraries. Gene, 1983. 25: p. 263–269.
32. Laemmli, U. K., Cleavage of structural proteins during the assembly of the head of bacteriophage T4. Nature, 1970. 227: p. 680–685.
33. Tai, M.-S., M. Mudgett-Hunter, and D. Levinson et al., A bifunctional fusion protein containing Fc-binding fragment B of staphylococcal protein A amino terminal to antidigoxin single-chain Fv. Biochemistry, 1990. 29: p. 8024–8030.
34. Marston, F. A. O., The purification of eukaryotic polypeptides synthesized in *Escherichia coli.* Biochemistry, 1986. 240: p. 1–12.
35. Roberts, T. M., Kacich, R., and Ptashne, M., A general method for maximizing the expression of a cloned gene. Proc. Natl. Acad. Sci. USA, 1979,76: p. 760–764.

What is claimed:

1. A method for inhibiting the growth of human tumor cells that express human EGF receptors and are mitogenically stimulated by EGF, the method comprising administering an effective amount of an anti-neoplastic agent and an effective amount of a monoclonal antibody to a human cancer patient having said tumor cells; (i) wherein said antibody binds to the extra-cellular domain of the human EGF receptor of said tumor cell; (ii) wherein the antibody is not conjugated to the anti-neoplastic agent; and (iii) wherein the antibody inhibit the binding of EGF to the EGF receptor.

2. A method for inhibiting the growth of human tumor cells that express human EGF receptors and are mitogenically stimulated by human EGF according to claim 1 wherein said anti-neoplastic agent is doxorubicin.

3. A method for inhibiting the growth of human tumor cells that express human EGF receptors and are mitogenically stimulated by human EGF according to claim 1 wherein said anti-neoplastic agent is cisplatin.

4. A method for inhibiting the growth of human tumor cells that express human EGF receptors and are mitogenically stimulated by human EGF according to claim 1 wherein said monoclonal antibody is 108 produced by hybridoma cell line ATCC HB 9764.

5. A method for inhibiting the growth of human tumor cells that express EGF receptors and are mitogenically stimulated by human EGF according to claim 1 wherein said monoclonal antibody is further characterized by its capability to inhibit the growth of human oral epidermoid carcinoma (KB) cells by binding to the extra-cellular domain of the human EGF receptor of said KB cells in an antigen-antibody complex.

6. A therapeutic composition comprising an amount of monoclonal antibody and an anti-neoplastic agent effective to inhibit the growth of human tumor cells that express human EGF receptors and are mitogenically stimulated by human EGF in association with a pharmaceutical carrier; (i) wherein the antibody binds to the extracellular domain of the human EGF receptor of the tumor cells; (ii) wherein the antibody is not conjugated to the anti-neoplastic agent; and (iii) wherein the antibody inhibits the binding of EGF to the EGF receptor.

7. A therapeutic composition according to claim 6 wherein said anti-neoplastic agent is doxorubicin.

8. A therapeutic composition according to claim 6 wherein said anti-neoplastic agent is cisplatin.

9. A therapeutic composition according to claim 6 wherein said monoclonal antibody is 108 produced by hybridoma cell line ATCC HB 9764.

* * * * *

UNITED STATES PATENT AND TRADEMARK OFFICE
CERTIFICATE OF CORRECTION

PATENT NO. : 6,217,866, B1  
DATED : April 17, 2001  
INVENTOR(S) : Schlessinger et al.

It is certified that error appears in the above-identified patent and that said Letters Patent is hereby corrected as shown below:

Column 10,  
Line 9, now reads "IgM(●—574)," should read -- IgM(●—●), --

Column 35,  
Line 48, now reads "inhibit" should read -- inhibits --

Signed and Sealed this

Eleventh Day of December, 2001

*Attest:*

NICHOLAS P. GODICI  
*Attesting Officer    Acting Director of the United States Patent and Trademark Office*

UNITED STATES PATENT AND TRADEMARK OFFICE
CERTIFICATE OF CORRECTION

PATENT NO.         : 6,217,866 B1
APPLICATION NO. : 08/487761
DATED                  : April 17, 2001
INVENTOR(S)         : Michael Sela, Esther Aboud-Pirak and Esther Hurwitz It is certified that error appears in the above-identified patent and that said Letters Patent is hereby corrected as shown below:

On the title page, item [75], inventors: Joseph Schlessinger, David Givol, Francoise Bellot, Richard Kris, George A. Ricca, Christopher Cheadle and Victoria J. South should be deleted and replaced with -- Michael Sela, Rehovot, Israel;

Esther Pirak, Tiveon, Israel;

Esther Hurwitz, Shoresh, Israel --.

On the title page, item [73], the assignee: "Rhone-Poulenc Rorer International (Holdings), Inc." should be deleted and replaced with -- Yeda Research and Development Company Ltd., Rehovot, Israel --

Signed and Sealed this

Fifth Day of August, 2008

JON W. DUDAS
*Director of the United States Patent and Trademark Office*

SEQUENCE LISTING (1) GENERAL INFORMATION:

(iii) NUMBER OF SEQUENCES: 17

(2) INFORMATION FOR SEQ ID NO:1:

(i) SEQUENCE CHARACTERISTICS:
      (A) LENGTH: 45 base pairs
      (B) TYPE: nucleic acid
      (C) STRANDEDNESS: double
      (D) TOPOLOGY: linear (ii) MOLECULE TYPE: other nucleic acid (xi) SEQUENCE DESCRIPTION: SEQ ID NO:1:

TCCGGAGGCG GTGGCTCGGG CGGTGGCGGC TCGGGTGGCG GCGGC    45

(2) INFORMATION FOR SEQ ID NO:2:

(i) SEQUENCE CHARACTERISTICS:
      (A) LENGTH: 15 amino acids
      (B) TYPE: amino acid
      (D) TOPOLOGY: linear (ii) MOLECULE TYPE: peptide (xi) SEQUENCE DESCRIPTION: SEQ ID NO:2:

Ser Gly Gly Gly Gly Ser Gly Gly Gly Gly Ser Gly Gly Gly Gly
1            5                  10               15

(2) INFORMATION FOR SEQ ID NO:3:

(i) SEQUENCE CHARACTERISTICS:
        (A) LENGTH: 12 base pairs
        (B) TYPE: nucleic acid
        (C) STRANDEDNESS: double
        (D) TOPOLOGY: linear (ii) MOLECULE TYPE: other nucleic acid (xi) SEQUENCE DESCRIPTION: SEQ ID NO:3:

ACCATGGATG TT                                                              12

(2) INFORMATION FOR SEQ ID NO:4:

(i) SEQUENCE CHARACTERISTICS:
        (A) LENGTH: 15 base pairs
        (B) TYPE: nucleic acid
        (C) STRANDEDNESS: double
        (D) TOPOLOGY: linear (ii) MOLECULE TYPE: other nucleic acid (xi) SEQUENCE DESCRIPTION: SEQ ID NO:4:

GCTGCATGAG GATCC                                                           15

(2) INFORMATION FOR SEQ ID NO:5:

(i) SEQUENCE CHARACTERISTICS:
        (A) LENGTH: 12 base pairs
        (B) TYPE: nucleic acid
        (C) STRANDEDNESS: double
        (D) TOPOLOGY: linear (ii) MOLECULE TYPE: other nucleic acid (xi) SEQUENCE DESCRIPTION: SEQ ID NO:5:

ACCATGGAAG TG                                                              12

(2) INFORMATION FOR SEQ ID NO:6:

(i) SEQUENCE CHARACTERISTICS:
        (A) LENGTH: 15 base pairs
        (B) TYPE: nucleic acid
        (C) STRANDEDNESS: double
        (D) TOPOLOGY: linear (ii) MOLECULE TYPE: other nucleic acid (xi) SEQUENCE DESCRIPTION: SEQ ID NO:6:

TCTGCATGAG GATCC                                                           15

(2) INFORMATION FOR SEQ ID NO:7:

(i) SEQUENCE CHARACTERISTICS:
        (A) LENGTH: 12 base pairs
        (B) TYPE: nucleic acid
        (C) STRANDEDNESS: double
        (D) TOPOLOGY: linear (ii) MOLECULE TYPE: other nucleic acid (xi) SEQUENCE DESCRIPTION: SEQ ID NO:7:

ACCATGGAAA TC                                                              12

(2) INFORMATION FOR SEQ ID NO:8:

(i) SEQUENCE CHARACTERISTICS:
        (A) LENGTH: 12 base pairs
        (B) TYPE: nucleic acid (C) STRANDEDNESS: double
        (D) TOPOLOGY: linear (ii) MOLECULE TYPE: other nucleic acid (xi) SEQUENCE DESCRIPTION: SEQ ID NO:8:

ACCATGCAGG TT                                                              12

(2) INFORMATION FOR SEQ ID NO:9:

(i) SEQUENCE CHARACTERISTICS:
        (A) LENGTH: 18 base pairs
        (B) TYPE: nucleic acid
        (C) STRANDEDNESS: double
        (D) TOPOLOGY: linear (ii) MOLECULE TYPE: other nucleic acid (xi) SEQUENCE DESCRIPTION: SEQ ID NO:9:

TCCTCCTAAT AAGGATCC                                                        18

(2) INFORMATION FOR SEQ ID NO:10:

(i) SEQUENCE CHARACTERISTICS:
        (A) LENGTH: 363 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 1..363

(xi) SEQUENCE DESCRIPTION: SEQ ID NO:10:

```
CAG GTT CAG CTG CAG CAG TCT GGA GCT GAG CTG ATG AAG CCT GGG GCC        48
Gln Val Gln Leu Gln Gln Ser Gly Ala Glu Leu Met Lys Pro Gly Ala
 1               5                  10                  15

TCA GTG AAG ATA TCC TGC AAG GCT ACT GGC TAC ACA TTC AGT AGT TAC        96
Ser Val Lys Ile Ser Cys Lys Ala Thr Gly Tyr Thr Phe Ser Ser Tyr
             20                  25                  30

TGG ATA GAG TGG GTA AAG CAG AGG CCT GGA CAT GGC CTT GAG TGG ATT       144
Trp Ile Glu Trp Val Lys Gln Arg Pro Gly His Gly Leu Glu Trp Ile
         35                  40                  45

GGA GAG ATT TTA CCG GGA AGT AAA AAA ACT AAC TAC AAT GAG AAG TTC       192
Gly Glu Ile Leu Pro Gly Ser Lys Lys Thr Asn Tyr Asn Glu Lys Phe
 50                  55                  60

AAG GGA AAG GCC ACA TTC ACT GCA GAT ACA TCC TCC AAC ACA GCC TAC       240
Lys Gly Lys Ala Thr Phe Thr Ala Asp Thr Ser Ser Asn Thr Ala Tyr
 65                  70                  75                  80

ATG CAA TTT AGC AGC CTG ACA TCT GAG GAC TCT GCC GTC TAT TAC TGT       288
Met Gln Phe Ser Ser Leu Thr Ser Glu Asp Ser Ala Val Tyr Tyr Cys
                 85                  90                  95

GCA AGA TAT TAC TAT AGG AAC GAC GAC TAT GGT ATG GAC TAC TGG GGT       336
Ala Arg Tyr Tyr Tyr Arg Asn Asp Asp Tyr Gly Met Asp Tyr Trp Gly
             100                 105                 110

CAA GGA ACC TCA GTC ACC GTC TCC TCA                                   363
Gln Gly Thr Ser Val Thr Val Ser Ser
        115                 120
```

(2) INFORMATION FOR SEQ ID NO:11:

(i) SEQUENCE CHARACTERISTICS:
        (A) LENGTH: 121 amino acids
        (B) TYPE: amino acid

```
        (D) TOPOLOGY: linear (ii) MOLECULE TYPE: protein (xi) SEQUENCE DESCRIPTION: SEQ ID NO:11:

Gln Val Gln Leu Gln Gln Ser Gly Ala Glu Leu Met Lys Pro Gly Ala
 1               5                  10                  15

Ser Val Lys Ile Ser Cys Lys Ala Thr Gly Tyr Thr Phe Ser Ser Tyr
            20                  25                  30

Trp Ile Glu Trp Val Lys Gln Arg Pro Gly His Gly Leu Glu Trp Ile
        35                  40                  45

Gly Glu Ile Leu Pro Gly Ser Lys Lys Thr Asn Tyr Asn Glu Lys Phe
50                  55                  60

Lys Gly Lys Ala Thr Phe Thr Ala Asp Thr Ser Ser Asn Thr Ala Tyr
65                  70                  75                  80

Met Gln Phe Ser Ser Leu Thr Ser Glu Asp Ser Ala Val Tyr Tyr Cys
                85                  90                  95

Ala Arg Tyr Tyr Tyr Arg Asn Asp Asp Tyr Gly Met Asp Tyr Trp Gly
            100                 105                 110

Gln Gly Thr Ser Val Thr Val Ser Ser
        115                 120

(2) INFORMATION FOR SEQ ID NO:12:

(i) SEQUENCE CHARACTERISTICS:
        (A) LENGTH: 336 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 1..336

(xi) SEQUENCE DESCRIPTION: SEQ ID NO:12:

GAA ATC CAC ATG ACA CAG ACT ACA TCC TCC CTG TCT GCC TCT CTG GGA      48
Glu Ile His Met Thr Gln Thr Thr Ser Ser Leu Ser Ala Ser Leu Gly
 1               5                  10                  15

GAC AGA GTC ACC ATC AGT TGC AGT GCA AGT CAG GAC ATC AGG AAT TAT      96
Asp Arg Val Thr Ile Ser Cys Ser Ala Ser Gln Asp Ile Arg Asn Tyr
            20                  25                  30

TTA AAC TGG TAT CAG CAG AAA CCT GAT GGA ACT GTT AAA CTC CTG ATC     144
Leu Asn Trp Tyr Gln Gln Lys Pro Asp Gly Thr Val Lys Leu Leu Ile
        35                  40                  45

TAT TAC ACA TCA ACT TTA CAT TCA GGA GTC CCA TCA AGG TTC AGT GGC     192
Tyr Tyr Thr Ser Thr Leu His Ser Gly Val Pro Ser Arg Phe Ser Gly
50                  55                  60

AGC GGG TCT GGG ACA GAT TAT TCT CTC ACC ATC AGC AAC CTG GAA CCT     240
Ser Gly Ser Gly Thr Asp Tyr Ser Leu Thr Ile Ser Asn Leu Glu Pro
65                  70                  75                  80

GAA GAT ATT GCC ACT TAT TAT TGT CAG CAG TAT AGT AAG ATT CCG TAC     288
Glu Asp Ile Ala Thr Tyr Tyr Cys Gln Gln Tyr Ser Lys Ile Pro Tyr
                85                  90                  95

ACG TTC ACA GGG GGG ACC AAG CTG GAA ATA AAA CGG GCT GAT GCT GCA     336
Thr Phe Thr Gly Gly Thr Lys Leu Glu Ile Lys Arg Ala Asp Ala Ala
            100                 105                 110

(2) INFORMATION FOR SEQ ID NO:13:

(i) SEQUENCE CHARACTERISTICS:
```

(A) LENGTH: 112 amino acids
        (B) TYPE: amino acid
        (D) TOPOLOGY: linear (ii) MOLECULE TYPE: protein (xi) SEQUENCE DESCRIPTION: SEQ ID NO:13:

```
Glu Ile His Met Thr Gln Thr Thr Ser Ser Leu Ser Ala Ser Leu Gly
 1               5                  10                  15

Asp Arg Val Thr Ile Ser Cys Ser Ala Ser Gln Asp Ile Arg Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Thr Leu His Ser Gly Val Pro Ser Arg Phe Ser Gly
50                  55                  60

Ser Gly Ser Gly Thr Asp Tyr Ser Leu Thr Ile Ser Asn Leu Glu Pro
65                  70                  75                  80

Glu Asp Ile Ala Thr Tyr Tyr Cys Gln Gln Tyr Ser Lys Ile Pro Tyr
                85                  90                  95

Thr Phe Thr Gly Gly Thr Lys Leu Glu Ile Lys Arg Ala Asp Ala Ala
            100                 105                 110
```

(2) INFORMATION FOR SEQ ID NO:14:

(i) SEQUENCE CHARACTERISTICS:
        (A) LENGTH: 354 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 1..354

(xi) SEQUENCE DESCRIPTION: SEQ ID NO:14:

```
GAA GTG CAG CTG GTG GAG TCT GGG GGA GGC TTA GTG AGG CCT GGA GGG      48
Glu Val Gln Leu Val Glu Ser Gly Gly Gly Leu Val Arg Pro Gly Gly
 1               5                  10                  15

TCC CTG AAA CTC TCC TGT GCA GCC TCT GGA TTC GCT TTC AGT AAC TAT      96
Ser Leu Lys Leu Ser Cys Ala Ala Ser Gly Phe Ala Phe Ser Asn Tyr
            20                  25                  30

GAC ATG TCT TGG GTT CGC CAG ACT CCG GAG AAG AGG CTG GAG TGG GTC     144
Asp Met Ser Trp Val Arg Gln Thr Pro Glu Lys Arg Leu Glu Trp Val
        35                  40                  45

GCG TAC ATT GGT AAT GGT GGT AAC ACC TAC TCT CCA GAC ACT GTG AAG     192
Ala Tyr Ile Gly Asn Gly Gly Asn Thr Tyr Ser Pro Asp Thr Val Lys
50                  55                  60

GGC CGA TTC ACC ATC TCC AGA GAC AAT GCC GAG AAC ACC CTA TAC CTT     240
Gly Arg Phe Thr Ile Ser Arg Asp Asn Ala Glu Asn Thr Leu Tyr Leu
65                  70                  75                  80

CAA ATG AGC AGT CTG AAG TCT GAG GAC ACA GCC ATT TAT TAC TGT GCA     288
Gln Met Ser Ser Leu Lys Ser Glu Asp Thr Ala Ile Tyr Tyr Cys Ala
                85                  90                  95

AGT CAC TAT GGT TAC GAC GGG AGG TTT GCT TAC TGG GGC CAA GGG ACT     336
Ser His Tyr Gly Tyr Asp Gly Arg Phe Ala Tyr Trp Gly Gln Gly Thr
            100                 105                 110

CTG GTC ACT GTC TCT GCA                                              354
Leu Val Thr Val Ser Ala
        115
```

(2) INFORMATION FOR SEQ ID NO:15:

(i) SEQUENCE CHARACTERISTICS:
        (A) LENGTH: 118 amino acids
        (B) TYPE: amino acid
        (D) TOPOLOGY: linear (ii) MOLECULE TYPE: protein (xi) SEQUENCE DESCRIPTION: SEQ ID NO:15:

```
Glu Val Gln Leu Val Glu Ser Gly Gly Gly Leu Val Arg Pro Gly Gly
 1               5                  10                  15

Ser Leu Lys Leu Ser Cys Ala Ala Ser Gly Phe Ala Phe Ser Asn Tyr
            20                  25                  30

Asp Met Ser Trp Val Arg Gln Thr Pro Glu Lys Arg Leu Glu Trp Val
        35                  40                  45

Ala Tyr Ile Gly Asn Gly Gly Asn Thr Tyr Ser Pro Asp Thr Val Lys
50                  55                  60

Gly Arg Phe Thr Ile Ser Arg Asp Asn Ala Glu Asn Thr Leu Tyr Leu
65                  70                  75                  80

Gln Met Ser Ser Leu Lys Ser Glu Asp Thr Ala Ile Tyr Tyr Cys Ala
                85                  90                  95

Ser His Tyr Gly Tyr Asp Gly Arg Phe Ala Tyr Trp Gly Gln Gly Thr
            100                 105                 110

Leu Val Thr Val Ser Ala
            115
```

(2) INFORMATION FOR SEQ ID NO:16:

(i) SEQUENCE CHARACTERISTICS:
        (A) LENGTH: 351 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 1..351

(xi) SEQUENCE DESCRIPTION: SEQ ID NO:16:

```
GAT GTT GTG ATG ACC CAA AGT CCA CTC TCC CTG CCT GTC AGT CTT GGA      48
Asp Val Val Met Thr Gln Ser Pro Leu Ser Leu Pro Val Ser Leu Gly
 1               5                  10                  15

GAT CAA GCC ACC ATC TCT TGC AGA TCT AGT CAG AGC CTT GAA CAC AGT      96
Asp Gln Ala Thr Ile Ser Cys Arg Ser Ser Gln Ser Leu Glu His Ser
            20                  25                  30

AAT GGA GAC ACC TAT TTA CAT TGG TAC CTG CAG AAG GCA GGC CAG TCT     144
Asn Gly Asp Thr Tyr Leu His Trp Tyr Leu Gln Lys Ala Gly Gln Ser
        35                  40                  45

CCA AAG CTC CTG ATC TAC AAA GTT TCC AAC CGA TTT TCT GGG GTC CCG     192
Pro Lys Leu Leu Ile Tyr Lys Val Ser Asn Arg Phe Ser Gly Val Pro
50                  55                  60

GAT AGG TTC AGT GGC AGT GGA TCA GGG ACA GAT TTC ACA CTC AAG ATC     240
Asp Arg Phe Ser Gly Ser Gly Ser Gly Thr Asp Phe Thr Leu Lys Ile
65                  70                  75                  80

AGC AGA GTG GAG GCT GAG GAT CTG GGA GTT TAT TTC TGC TGT CAA AGT     288
Ser Arg Val Glu Ala Glu Asp Leu Gly Val Tyr Phe Cys Cys Gln Ser
                85                  90                  95

ACA CAT GTT CCG TGG ACG TTC GGT GGA GGC ACC AAC CTG GAA ATC AAA     336
Thr His Val Pro Trp Thr Phe Gly Gly Gly Thr Asn Leu Glu Ile Lys
            100                 105                 110
```

-continued

```
CGG GCT GAT GCT GCA                                              351
Arg Ala Asp Ala Ala
        115
```

(2) INFORMATION FOR SEQ ID NO:17:

(i) SEQUENCE CHARACTERISTICS:
        (A) LENGTH: 117 amino acids
        (B) TYPE: amino acid
        (D) TOPOLOGY: linear (ii) MOLECULE TYPE: protein (xi) SEQUENCE DESCRIPTION: SEQ ID NO:17:

```
Asp Val Val Met Thr Gln Ser Pro Leu Ser Leu Pro Val Ser Leu Gly
 1               5                  10                  15

Asp Gln Ala Thr Ile Ser Cys Arg Ser Ser Gln Ser Leu Glu His Ser
                20                  25                  30

Asn Gly Asp Thr Tyr Leu His Trp Tyr Leu Gln Lys Ala Gly Gln Ser
            35                  40                  45

Pro Lys Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Cys Gln Ser
                85                  90                  95

Thr His Val Pro Trp Thr Phe Gly Gly Gly Thr Asn Leu Glu Ile Lys
                100                 105                 110

Arg Ala Asp Ala Ala
        115
```